US009078904B2

(12) United States Patent
Mulligan-Kehoe

(10) Patent No.: US 9,078,904 B2
(45) Date of Patent: Jul. 14, 2015

(54) METHODS FOR INCREASING PLASMIN ACTIVITY AND PROMOTING PLAQUE REGRESSION IN THE TREATMENT OF ATHEROSCLEROSIS

(75) Inventor: Mary Jo Mulligan-Kehoe, Enfield, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/982,830

(22) PCT Filed: Feb. 3, 2012

(86) PCT No.: PCT/US2012/023714
§ 371 (c)(1),
(2), (4) Date: Jul. 31, 2013

(87) PCT Pub. No.: WO2012/109097
PCT Pub. Date: Aug. 16, 2012

(65) Prior Publication Data
US 2013/0310305 A1 Nov. 21, 2013

Related U.S. Application Data

(60) Provisional application No. 61/441,301, filed on Feb. 10, 2011.

(51) Int. Cl.
| | |
|---|---|
| *A61K 38/57* | (2006.01) |
| *A61K 38/48* | (2006.01) |
| *C07K 14/81* | (2006.01) |
| *A61K 38/55* | (2006.01) |
| *C07K 14/47* | (2006.01) |
| *A61K 38/17* | (2006.01) |
| *A61K 38/42* | (2006.01) |
| *A61K 35/16* | (2015.01) |
| *C07K 14/775* | (2006.01) |
| *A61K 38/00* | (2006.01) |
| *C07K 14/745* | (2006.01) |

(52) U.S. Cl.
CPC ............ *A61K 38/57* (2013.01); *A61K 38/484* (2013.01); *A61K 38/55* (2013.01); *C07K 14/81* (2013.01); *C07K 14/811* (2013.01); *C07K 14/8132* (2013.01); *A01K 2217/05* (2013.01); *A61K 35/16* (2013.01); *A61K 38/00* (2013.01); *A61K 38/177* (2013.01); *A61K 38/1709* (2013.01); *A61K 38/42* (2013.01); *C07K 14/47* (2013.01); *C07K 14/745* (2013.01); *C07K 14/775* (2013.01)

(58) Field of Classification Search
None
See application file for complete search history.

(56) References Cited

U.S. PATENT DOCUMENTS

| | | | |
|---|---|---|---|
| 6,008,020 A | 12/1999 | Hastings et al. | 435/69.2 |
| 7,510,714 B2 * | 3/2009 | Mulligan-Kehoe et al. | 424/184.1 |
| 2002/0143165 A1 | 10/2002 | Lawrence et al. | 536/23.1 |
| 2007/0191277 A1 * | 8/2007 | Mulligan-Kehoe et al. | 514/12 |

FOREIGN PATENT DOCUMENTS

WO    WO 03/071267 A1    8/2003

OTHER PUBLICATIONS

Drinane, et al., "The Antiangiogenic Activity of rPAI-1(23) Inhibits Vasa Vasorum and Growth of Atherosclerotic Plaque," Circ. Res. 104:337-345 (2009).*
Mollmark, et al., "Antiangiogenesis Activity of rPAI-1(23) Promotes Vasa Vasorum Regression in Hypercholesterolemic Mice Through a Plasmin-Dependent Mechanism," Circ. Res. 108:1419-1428 (2011).*
Mulligan-Kehoe et al., "A Truncated Plasminogen Activator Inhibitor-1 Protein Blocks the Availability of Heparin-binding Vascular Endothelial Growth Factor a Isoforms," J. Biol. Chem. 277:49077-49089 (2002).*
Bobik, A. and Tkachuk, V. "Metalloproteinases and Plasminogen Activators in Vessel Remodeling" Current Hypertension Reports 2003 5:466-472.
Cheresh et al. "Recognition of Distinct Adhesive Sites on Fibrinogen by Related Integrins on Platelets and Endothelial Cells" Cell 1989 58:945-953.
Davis, G.E. and Saunders, W.B. "Molecular Balance of Capillary Tube Formation versus Regression in Wound Repair: Role of Matrix Metalloproteinases and their Inhibitors" Journal of Investigative Dermatology Symposium Proceedings 2006 11:44-56.
Davis, G.E. and Senger, D.R. "Endothelial Extracellular Matrix Biosynthesis, Remodeling, and Functions During Vascular Morphogenesis and Neovessel Stabilization" Circulation Research 2005 97:1093-1107.
Davis et al. "Matrix Metalloproteinase-1 and -9 Activation by Plasmin Regulates a Novel Endothelial Cell-Mediated Mechanism of Collagen Gel Contraction and Capillary Tube Regression in Three-Dimensional Collagen Matrices" Journal of Cell Science 2000 114:917-930.

(Continued)

*Primary Examiner* — James H Alstrum Acevedo
*Assistant Examiner* — Thea D'Ambrosio
(74) *Attorney, Agent, or Firm* — Licata & Tyrrell P.C.

(57) ABSTRACT

The present invention provides the use of recombinant plasminogen activator inhibitor-1 (PAI-1) isoform 23 in methods of increasing plasmin activity, inhibiting angiogenic vasa vasorum, promoting plaque regression and treating atherosclerosis by administering to a subject in need of treatment an effective amount of recombinant plasminogen activator inhibitor type isoform 23 (rPAI-123). In some embodiments, rPAI-123 is set forth in SEQ ID NOs:5-8. In other embodiments, rPAI-123 is administered at a dose in the range of approximately 2.5 μg/kg/day to 20 μg/kg/day. In further embodiments, the effective amount achieves a ratio of rPAI-123 to PAI-1 is in the range of approximately 1:2 to 3:1.

3 Claims, 4 Drawing Sheets

(56) References Cited

OTHER PUBLICATIONS

Dellas, C. and Loskutoff, D.J. "Historical Analysis of PAI-I from Its Discovery to Its Potential Role in Cell Motility and Disease" Thrombosis and Haemostasis 2005 93:631-640.

Drinane et al. "The Anti-Angiogenic Activity of rPAI-1$_{23}$ Inhibits Fibroblast Growth Factor-2 Functions" The Journal of Biological Chemistry 2006 281(44):33336-33344.

Drinane et al. "The Antiangiogenic Activity of rPAI-123 Inhibits Vasa Vasorum and Growth of Atherosclerotic Plaque" Circulation Research 2009 104:337-345.

Dvorak et al. "Vascular Permeability Factor, Fibrin, and the Pathogenesis of Tumor Stroma Formation" Annals of the New York Academy of Sciences 1992 667:101-111.

Garcia-Touchard et al. "Extracellular Proteases in Atherosclerosis and Restenosis" Arteriosclerosis, Thrombosis, and Vascular Biology 2005 25:1119-1127.

Heistad, D.D. and Marcus, M.L. "Role of Vasa Vasorum in Nourishment of the Aorta" Blood Vessels 1979 16:225-238.

Khurana et al "Angiogenesis-Dependent and Independent Phases of Intimal Hyperplasia" Circulation 2004 110:2436-2443.

Langheinrich et al. "Correlation of Vasa Vasorum Neovascularization and Plaque Progression in Aortas of Apolipoprotein E$^{-/-}$/Low-Density Lipoprotein$^{-/-}$ Double Knockout Mice" Arteriosclerosis, Thrombosis, and Vascular Biology 2006 26:347-352.

Langheinrich et al. "Vasa Vasorum Neovascularization and Lesion Distribution Among Different Vascular Beds in ApoE$^{-/-}$/LDL$^{-/-}$ Double Knockout Mice" Atherosclerosis 2007 191:73-81.

Mayer et al. "Sites of Nidogen Cleavage by Proteases Involved in Tissue Homeostasis and Remodelling" European Journal of Biochemistry 1993 217:877-884.

Mosesson, M.W. "Fibrinogen and Fibrin Structure and Functions" Journal of Thrombosis and Haemostasis 2005 3:1894-1904.

Moulton et al. "Angiogenesis Inhibitors Endostatin or TNP-470 Reduce Intimal Neovascularization and Plaque Growth in Apolipoprotein E-Deficient Mice" Circulation 1999 99:1726-1732.

Moulton et al. "Inhibition of Plaque Neovascularization Reduces Macrophage Accumulation and Progression of Advanced Atherosclerosis" Proceedings of the National Academy of Sciences 2003 100(8):4736-4741.

Mulligan-Kehoe et al. "A Truncated Plasminogen Activator Inhibitor-1 Protein Blocks the Availability of Heparin-Binding Vascular Endothelial Growth Factor a Isoforms" The Journal of Biological Chemistry 2002 277(50):49077-49089.

Mulligan-Kehoe et al. "A Truncated Plasminogen Activator Inhibitor-1 Protein Induces and Inhibits Angiostatin (Kringles 1-3), a Plasminogen Cleavage Product" The Journal of Biological Chemistry 2001 276(11):8588-8596.

Nagy et al. "Pathogenesis of Tumor Stroma Generation: A Critical Role for Leaky Blood Vessels and Fibrin Deposition" Biochimica et Biophysica Acta 1988 948:305-326.

O'Brien et al. "Angiogenesis in Human Coronary Atherosclerotic Plaques" American Journal of Pathology 1994 145(4):883-894.

O'Reilly et al. "Angiostatin: A Novel Angiogenesis Inhibitor that Mediates the Suppression of Metastases by a Lewis Lung Carcinoma" Cell 1994 79:315-328.

O'Reilly et al. "Endostatin: An Endogenous Inhibitor of Angiogenesis and Tumor Growth" Cell 1997 88:277-285.

Pepper, M.S. "Role of the Matrix Metalloproteinase and Plasminogen Activator—Plasmin Systems in Angiogenesis" Arteriosclerosis, Thrombosis, and Vascular Biology 2001 21:1104-1117.

Rhodes, J.M. and Simons, M. "The Extracellular Matrix and Blood Vessel Formation: Not Just a Scaffold" Journal of Cellular and Molecular Medicine 2007 11(2):176-205.

Sahni, A. and Francis, C.W. "Plasmic Degradation Modulates Activity of Fibrinogen-Bound Fibroblast Growth Factor-2" Journal of Thrombosis and Haemostasis 2003 1:1271-1277.

Saunders et al. "MMP-1 Activation by Serine Proteases and MMP-10 Induces Human Capillary Tubular Network Collapse and Regression in 3D Collagen Matrices" Journal of Cell Science 2005 118:2325-2340.

Seiffert et al. "Interactions Between Type 1 Plasminogen Activator Inhibitor, Extracellular Matrix and Vitronectin" Cell Differentiation and Development 1990 32:287-292.

Senger, D.R. "Molecular Framework for Angiogenesis a Complex Web of Interactions Between Extravasated Plasma Proteins and Endothelial Cell Proteins Induced by Angiogenic Cytokines" American Journal of Pathology 1996 149(1):1-7.

Suehiro et al. "Fibrinogen Is a Ligand for Integrin $\alpha_5\beta_1$ on Endothelial Cells" The Journal of Biological Chemistry 1997 272(8):5360-5366.

Vernon, R.B. and Sage, E.H. "Between Molecules and Morphology Extracellular Matrix and Creation of Vascular Form" American Journal of Pathology 1995 147(4):873-883.

Virmani et al. "Atherosclerotic Plaque Progression and Vulnerability to Rupture" Arteriosclerosis, Thrombosis, and Vascular Biology 2005 25:2054-2061.

Werb, Z. "ECM and Cell Surface Proteolysis: Regulating Cellular Ecology" Cell 1997 91:439-442.

Whitelock et al. "The Degradation of Human Endothelial Cell-Derived Perlecan and Release of Bound Basic Fibroblast Growth Factor by Stromelysin, Collagenase, Plasmin, and Heparanases" The Journal of Biological Chemistry 1996 271(17):10079-10086.

International Search Report from PCT/US2012/023714, Jun. 29, 2012.

International Preliminary Report on Patentability from PCT/US2012/023714, Aug. 22, 2013.

* cited by examiner

SEQUENCE LISTING

```
<160> NUMBER OF SEQ ID NOS: 8

<210> SEQ ID NO 1
<211> LENGTH: 402
<212> TYPE: PRT
<213> ORGANISM: Sus scrofa

<400> SEQUENCE: 1

Met Arg Met Ser Leu Val Phe Ala Cys Leu Ala Met Gly Leu Ala Leu
1               5                   10                  15

Thr Phe Ala Glu Gly Ser Ala Ser Ser His His Gln Ser Leu Ala Ala
            20                  25                  30

Arg Leu Ala Thr Asp Phe Gly Val Lys Val Phe Arg Gln Val Val Gln
        35                  40                  45

Ala Ser Lys Asp Arg Asn Val Val Phe Ser Pro Tyr Gly Val Ala Ser
    50                  55                  60

Val Leu Ala Met Leu Gln Leu Thr Thr Ala Gly Asp Thr Gln Gln Gln
65                  70                  75                  80

Ile Gln Glu Ala Met Gln Phe Lys Ile Glu Glu Lys Gly Met Ala Pro
                85                  90                  95

Ala Leu Arg Gln Leu Tyr Lys Glu Leu Met Gly Pro Trp Asn Lys Asp
            100                 105                 110

Glu Ile Ser Thr Ala Asp Ala Ile Phe Val Gln Arg Asp Leu Lys Leu
        115                 120                 125

Val Gln Gly Phe Met Pro Tyr Phe Phe Arg Leu Phe Arg Thr Thr Val
    130                 135                 140

Lys Gln Val Asp Phe Ser Glu Met Asp Arg Ala Arg Phe Ile Ile Asn
145                 150                 155                 160

Asp Trp Val Lys Arg His Thr Lys Gly Met Ile Asn Asp Leu Leu Gly
                165                 170                 175

Gln Gly Ala Val Asp Gln Leu Thr Arg Leu Val Leu Val Asn Ala Leu
            180                 185                 190

Tyr Phe Asn Gly Gln Trp Lys Thr Pro Phe Pro Glu Lys Ser Thr His
        195                 200                 205
```

His Arg Leu Phe His Lys Ser Asp Gly Ser Thr Val Ser Val Pro Met
            210                 215                 220

Met Ala Gln Thr Asn Lys Phe Asn Tyr Thr Glu Phe Ser Thr Pro Asp
225                 230                 235                 240

Gly His Tyr Tyr Asp Ile Leu Glu Leu Pro Tyr His Gly Asn Thr Leu
                245                 250                 255

Ser Met Phe Ile Ala Ala Pro Tyr Glu Lys Glu Val Pro Leu Ser Ala
            260                 265                 270

Leu Thr Ser Ile Leu Asp Ala Gln Leu Ile Ser Gln Trp Lys Gly Asn
        275                 280                 285

Met Thr Arg Leu Thr Arg Leu Leu Val Leu Pro Lys Phe Ser Leu Glu
290                 295                 300

Ser Glu Val Asp Leu Arg Arg Pro Leu Glu Asn Leu Gly Met Thr Asp
305                 310                 315                 320

Met Phe Arg Pro Asn Gln Ala Asp Phe Ser Ser Leu Ser Asp Gln Glu
                325                 330                 335

Leu Leu Tyr Met Ser Gln Ala Leu Gln Lys Val Lys Ile Glu Val Asn
            340                 345                 350

Glu Ser Gly Thr Val Ala Ser Ser Thr Ala Ile Ile Val Ser Ala
        355                 360                 365

Arg Met Ala Pro Glu Glu Ile Ile Met Asp Arg Pro Phe Leu Phe Val
370                 375                 380

Val Arg His Asn Pro Thr Gly Thr Val Leu Phe Met Gly Gln Val Met
385                 390                 395                 400

Glu Pro

<210> SEQ ID NO 2
<211> LENGTH: 402
<212> TYPE: PRT
<213> ORGANISM: Bos taurus

<400> SEQUENCE: 2

Met Arg Met Ser Pro Val Phe Ala Cys Leu Ala Leu Gly Leu Ala Leu
1               5                   10                  15

Ile Phe Gly Glu Gly Ser Ala Ser Tyr Gln Pro Gln Ser Ala Ala Ala
            20                  25                  30

Ser Leu Ala Thr Asp Phe Gly Val Lys Val Phe Gln Gln Val Val Arg
        35                  40                  45

Ala Ser Lys Asp Arg Asn Val Val Phe Ser Pro Tyr Gly Val Ala Ser
50                  55                  60

Val Leu Ala Met Leu Gln Leu Thr Thr Gly Gly Glu Thr Arg Gln Gln
65                  70                  75                  80

Ile Gln Glu Ala Met Gln Phe Lys Ile Glu Glu Lys Gly Met Ala Pro
                85                  90                  95

Ala Phe His Arg Leu Tyr Lys Glu Leu Met Gly Pro Trp Asn Lys Asp
            100                 105                 110

Glu Ile Ser Thr Ala Asp Ala Ile Phe Val Gln Arg Asp Leu Glu Leu
        115                 120                 125

Val His Gly Phe Met Pro Asn Phe Phe Arg Leu Phe Arg Thr Thr Val
    130                 135                 140

Lys Gln Val Asp Phe Ser Glu Val Glu Arg Ala Arg Phe Ile Val Asn
145                 150                 155                 160

Asp Trp Val Lys Arg His Thr Lys Gly Met Ile Ser Asp Leu Leu Gly
                165                 170                 175

```
Glu Gly Ala Val Asp Gln Leu Thr Arg Leu Val Leu Val Asn Ala Leu
            180                 185                 190

Tyr Phe Asn Gly Gln Trp Lys Met Pro Phe Pro Glu Ser Asn Thr His
        195                 200                 205

His Arg Leu Phe His Lys Ser Asp Gly Ser Thr Ile Ser Val Pro Met
210                 215                 220

Met Ala Gln Thr Asn Lys Phe Asn Tyr Thr Glu Phe Thr Thr Pro Asp
225                 230                 235                 240

Gly Arg Tyr Tyr Asp Ile Leu Glu Leu Pro Tyr His Gly Asn Thr Leu
                245                 250                 255

Ser Met Leu Ile Ala Ala Pro Tyr Glu Lys Glu Val Pro Leu Ser Ala
            260                 265                 270

Leu Thr Ser Ile Leu Asp Ala Glu Leu Ile Ser Gln Trp Lys Gly Asn
        275                 280                 285

Met Thr Arg Leu Thr Arg Leu Leu Val Leu Pro Lys Phe Ser Leu Glu
290                 295                 300

Thr Glu Ile Asp Leu Arg Arg Pro Leu Glu Asn Leu Gly Met Thr Asp
305                 310                 315                 320

Met Phe Arg Pro Ser Gln Ala Asp Phe Ser Ser Phe Ser Asp Gln Glu
                325                 330                 335

Phe Leu Tyr Val Ser Gln Ala Leu Gln Lys Val Lys Ile Glu Val Asn
            340                 345                 350

Glu Ser Gly Thr Leu Ala Ser Ser Ser Thr Ala Leu Val Val Ser Ala
        355                 360                 365

Arg Met Ala Pro Glu Glu Ile Ile Met Asp Arg Pro Phe Leu Phe Val
370                 375                 380

Val Arg His Asn Pro Thr Gly Thr Val Leu Phe Met Gly Gln Val Met
385                 390                 395                 400

Glu Pro

<210> SEQ ID NO 3
<211> LENGTH: 402
<212> TYPE: PRT
<213> ORGANISM: Homo sapiens

<400> SEQUENCE: 3

Met Gln Met Ser Pro Ala Leu Thr Cys Leu Val Leu Gly Leu Ala Leu
1               5                   10                  15

Val Phe Gly Glu Gly Ser Ala Val His His Pro Pro Ser Tyr Val Ala
            20                  25                  30

His Leu Ala Ser Asp Phe Gly Val Arg Val Phe Gln Gln Val Ala Gln
        35                  40                  45

Ala Ser Lys Asp Arg Asn Val Val Phe Ser Pro Tyr Gly Val Ala Ser
    50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
        115                 120                 125

Val Gln Gly Phe Met Pro His Phe Phe Arg Leu Phe Arg Ser Thr Val
    130                 135                 140
```

```
Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
            165                 170                 175

Lys Gly Ala Val Asp Gln Leu Thr Arg Leu Val Leu Val Asn Ala Leu
        180                 185                 190

Tyr Phe Asn Gly Gln Trp Lys Thr Pro Phe Pro Asp Ser Ser Thr His
    195                 200                 205

Arg Arg Leu Phe His Lys Ser Asp Gly Ser Thr Val Ser Val Pro Met
210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Leu Val Leu Pro Lys Phe Ser Leu Glu
    290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Thr Ala Val Ile Val Ser Ala
        355                 360                 365

Arg Met Ala Pro Glu Glu Ile Ile Met Asp Arg Pro Phe Leu Phe Val
    370                 375                 380

Val Arg His Asn Pro Thr Gly Thr Val Leu Phe Met Gly Gln Val Met
385                 390                 395                 400

Glu Pro

<210> SEQ ID NO 4
<211> LENGTH: 402
<212> TYPE: PRT
<213> ORGANISM: Mus musculus

<400> SEQUENCE: 4

Met Gln Met Ser Ser Ala Leu Ala Cys Leu Ile Leu Gly Leu Val Leu
1               5                   10                  15

Val Ser Gly Lys Gly Phe Thr Leu Pro Leu Arg Glu Ser His Thr Ala
            20                  25                  30

His Gln Ala Thr Asp Phe Gly Val Lys Val Phe Gln Gln Val Val Gln
        35                  40                  45

Ala Ser Lys Asp Arg Asn Val Val Phe Ser Pro Tyr Gly Val Ser Ser
    50                  55                  60

Val Leu Ala Met Leu Gln Met Thr Thr Ala Gly Lys Thr Arg Arg Gln
65                  70                  75                  80

Ile Gln Asp Ala Met Gly Phe Lys Val Asn Glu Lys Gly Thr Ala His
                85                  90                  95

Ala Leu Arg Gln Leu Ser Lys Glu Leu Met Gly Pro Trp Asn Lys Asn
            100                 105                 110
```

```
Glu Ile Ser Thr Ala Asp Ala Ile Phe Val Gln Arg Asp Leu Glu Leu
            115                 120                 125

Val Gln Gly Phe Met Pro His Phe Phe Lys Leu Phe Gln Thr Met Val
        130                 135                 140

Lys Gln Val Asp Phe Ser Glu Val Arg Ala Arg Phe Ile Ile Asn
145                 150                 155                 160

Asp Trp Val Glu Arg His Thr Lys Gly Met Ile Ser Asp Leu Leu Ala
                165                 170                 175

Lys Gly Ala Val Asp Glu Leu Thr Arg Leu Val Leu Val Asn Ala Leu
            180                 185                 190

Tyr Phe Ser Gly Gln Trp Lys Thr Pro Phe Leu Glu Ala Ser Thr His
        195                 200                 205

Gln Arg Leu Phe His Lys Ser Asp Gly Ser Thr Val Ser Val Pro Met
    210                 215                 220

Met Ala Gln Ser Asn Lys Phe Asn Tyr Thr Glu Phe Thr Thr Pro Asp
225                 230                 235                 240

Gly Leu Glu Tyr Asp Val Val Glu Leu Pro Tyr Gln Gly Asp Thr Leu
                245                 250                 255

Ser Met Phe Ile Ala Ala Pro Phe Glu Lys Asp Val His Leu Ser Ala
            260                 265                 270

Leu Thr Asn Ile Leu Asp Ala Glu Leu Ile Arg Gln Trp Lys Gly Asn
        275                 280                 285

Met Thr Arg Leu Pro Arg Leu Leu Ile Leu Pro Lys Phe Ser Leu Glu
    290                 295                 300

Thr Glu Val Asp Leu Arg Gly Pro Leu Glu Lys Leu Gly Met Pro Asp
305                 310                 315                 320

Met Phe Ser Ala Thr Leu Ala Asp Phe Thr Ser Leu Ser Asp Gln Glu
                325                 330                 335

Gln Leu Ser Val Ala Gln Ala Leu Gln Lys Val Arg Ile Glu Val Asn
            340                 345                 350

Glu Ser Gly Thr Val Ala Ser Ser Thr Ala Phe Val Ile Ser Ala
        355                 360                 365

Arg Met Ala Pro Thr Glu Met Val Ile Asp Arg Ser Phe Leu Phe Val
    370                 375                 380

Val Arg His Asn Pro Thr Glu Thr Ile Leu Phe Met Gly Gln Val Met
385                 390                 395                 400

Glu Pro

<210> SEQ ID NO 5
<211> LENGTH: 181
<212> TYPE: PRT
<213> ORGANISM: Sus scrofa

<400> SEQUENCE: 5

Met Gly Pro Trp Asn Lys Asp Glu Ile Ser Thr Ala Asp Ala Ile Phe
1               5                   10                  15

Val Gln Arg Asp Leu Lys Leu Val Gln Gly Phe Met Pro Tyr Phe Phe
            20                  25                  30

Arg Leu Phe Arg Thr Thr Val Lys Gln Val Asp Phe Ser Glu Met Asp
        35                  40                  45

Arg Ala Arg Phe Ile Ile Asn Asp Trp Val Lys Arg His Thr Lys Gly
    50                  55                  60

Met Ile Asn Asp Leu Leu Gly Gln Gly Ala Val Asp Gln Leu Thr Arg
65                  70                  75                  80
```

```
Leu Val Leu Val Asn Ala Leu Tyr Phe Asn Gly Gln Trp Lys Thr Pro
                85                  90                  95

Phe Pro Glu Lys Ser Thr His His Arg Leu Phe His Lys Ser Asp Gly
            100                 105                 110

Ser Thr Val Ser Val Pro Met Met Ala Gln Thr Asn Lys Phe Asn Tyr
        115                 120                 125

Thr Glu Phe Ser Thr Pro Asp Gly His Tyr Tyr Asp Ile Leu Glu Leu
    130                 135                 140

Pro Tyr His Gly Asn Thr Leu Ser Met Phe Ile Ala Ala Pro Tyr Glu
145                 150                 155                 160

Lys Glu Val Pro Leu Ser Ala Leu Thr Ser Ile Leu Asp Ala Gln Leu
                165                 170                 175

Ile Ser Gln Trp Lys
            180

<210> SEQ ID NO 6
<211> LENGTH: 181
<212> TYPE: PRT
<213> ORGANISM: Bos taurus

<400> SEQUENCE: 6

Met Gly Pro Trp Asn Lys Asp Glu Ile Ser Thr Ala Asp Ala Ile Phe
1               5                   10                  15

Val Gln Arg Asp Leu Glu Leu Val His Gly Phe Met Pro Asn Phe Phe
            20                  25                  30

Arg Leu Phe Arg Thr Thr Val Lys Gln Val Asp Phe Ser Glu Val Glu
        35                  40                  45

Arg Ala Arg Phe Ile Val Asn Asp Trp Val Lys Arg His Thr Lys Gly
    50                  55                  60

Met Ile Ser Asp Leu Leu Gly Glu Gly Ala Val Asp Gln Leu Thr Arg
65                  70                  75                  80

Leu Val Leu Val Asn Ala Leu Tyr Phe Asn Gly Gln Trp Lys Met Pro
                85                  90                  95

Phe Pro Glu Ser Asn Thr His His Arg Leu Phe His Lys Ser Asp Gly
            100                 105                 110

Ser Thr Ile Ser Val Pro Met Met Ala Gln Thr Asn Lys Phe Asn Tyr
        115                 120                 125

Thr Glu Phe Thr Thr Pro Asp Gly Arg Tyr Tyr Asp Ile Leu Glu Leu
    130                 135                 140

Pro Tyr His Gly Asn Thr Leu Ser Met Leu Ile Ala Ala Pro Tyr Glu
145                 150                 155                 160

Lys Glu Val Pro Leu Ser Ala Leu Thr Ser Ile Leu Asp Ala Glu Leu
                165                 170                 175

Ile Ser Gln Trp Lys
            180

<210> SEQ ID NO 7
<211> LENGTH: 181
<212> TYPE: PRT
<213> ORGANISM: Homo sapiens

<400> SEQUENCE: 7

Met Gly Pro Trp Asn Lys Asp Glu Ile Ser Thr Thr Asp Ala Ile Phe
1               5                   10                  15

Val Gln Arg Asp Leu Lys Leu Val Gln Gly Phe Met Pro His Phe Phe
            20                  25                  30
```

-continued

```
Arg Leu Phe Arg Ser Thr Val Lys Gln Val Asp Phe Ser Glu Val Glu
                35                  40                  45

Arg Ala Arg Phe Ile Ile Asn Asp Trp Val Lys Thr His Thr Lys Gly
         50                  55                  60

Met Ile Ser Asn Leu Leu Gly Lys Gly Ala Val Asp Gln Leu Thr Arg
 65                  70                  75                  80

Leu Val Leu Val Asn Ala Leu Tyr Phe Asn Gly Gln Trp Lys Thr Pro
                 85                  90                  95

Phe Pro Asp Ser Ser Thr His Arg Arg Leu Phe His Lys Ser Asp Gly
                100                 105                 110

Ser Thr Val Ser Val Pro Met Met Ala Gln Thr Asn Lys Phe Asn Tyr
            115                 120                 125

Thr Glu Phe Thr Thr Pro Asp Gly His Tyr Tyr Asp Ile Leu Glu Leu
        130                 135                 140

Pro Tyr His Gly Asp Thr Leu Ser Met Phe Ile Ala Ala Pro Tyr Glu
145                 150                 155                 160

Lys Glu Val Pro Leu Ser Ala Leu Thr Asn Ile Leu Ser Ala Gln Leu
                165                 170                 175

Ile Ser His Trp Lys
            180

<210> SEQ ID NO 8
<211> LENGTH: 181
<212> TYPE: PRT
<213> ORGANISM: Mus musculus

<400> SEQUENCE: 8

Met Gly Pro Trp Asn Lys Asn Glu Ile Ser Thr Ala Asp Ala Ile Phe
 1               5                  10                  15

Val Gln Arg Asp Leu Glu Leu Val Gln Gly Phe Met Pro His Phe Phe
                20                  25                  30

Lys Leu Phe Gln Thr Met Val Lys Gln Val Asp Phe Ser Glu Val Glu
            35                  40                  45

Arg Ala Arg Phe Ile Ile Asn Asp Trp Val Glu Arg His Thr Lys Gly
         50                  55                  60

Met Ile Ser Asp Leu Leu Ala Lys Gly Ala Val Asp Glu Leu Thr Arg
 65                  70                  75                  80

Leu Val Leu Val Asn Ala Leu Tyr Phe Ser Gly Gln Trp Lys Thr Pro
                 85                  90                  95

Phe Leu Glu Ala Ser Thr His Gln Arg Leu Phe His Lys Ser Asp Gly
                100                 105                 110

Ser Thr Val Ser Val Pro Met Met Ala Gln Ser Asn Lys Phe Asn Tyr
            115                 120                 125

Thr Glu Phe Thr Thr Pro Asp Gly Leu Glu Tyr Asp Val Val Glu Leu
        130                 135                 140

Pro Tyr Gln Gly Asp Thr Leu Ser Met Phe Ile Ala Ala Pro Phe Glu
145                 150                 155                 160

Lys Asp Val His Leu Ser Ala Leu Thr Asn Ile Leu Asp Ala Glu Leu
                165                 170                 175

Ile Arg Gln Trp Lys
            180
```

METHODS FOR INCREASING PLASMIN ACTIVITY AND PROMOTING PLAQUE REGRESSION IN THE TREATMENT OF ATHEROSCLEROSIS

INTRODUCTION

This patent application is a U.S. National Stage Application of PCT/US2012/023714 filed Feb. 3, 2012 and claims the benefit of priority from U.S. Provisional Application Ser. No. 61/441,301, filed Feb. 10, 2011, the contents of each of which are incorporated herein by reference in their entirety.

This invention was made with government support under contract number HL69948 awarded by the National Institutes of Health. The government has certain rights in the invention.

BACKGROUND OF THE INVENTION

The vasa vasorum are a network of microvasculature that originate primarily in the adventitia of large arteries (Heistad & Marcus (1979) *Blood Vessels* 16(5):225-238). Neovascularized second order vasa vasorum are associated with more advanced stages of human atherosclerosis (O'Brien, et al. (1994) *Am. J. Pathol.* 145(4):883-894; Virmani, et al. (2005) *Arterioscler. Thromb. Vasc. Biol.* 25(10):2054-2061). The presence and extent of vasa vasorum correlate with atherosclerotic lesion size and lumen diameter in hypercholesterolemic animal models (Heistad & Marcus (1979) supra; Khurana, et al. (2004) *Circulation* 110(16):2436-2443; Langheinrich, et al. (2007) *Atherosclerosis* 191(1):73-81; Langheinrich, et al. (2006) *Arterioscler. Thromb. Vasc. Biol.* 26(2): 347-352; Moulton, et al. (2003) *Proc. Natl. Acad. Sci. USA* 100(8):4736-4741). It has been demonstrated that anti-angiogenic proteins inhibit neovascularization of the vasa vasorum and associated plaque progression in genetically modified mouse models of atherosclerosis (Moulton, et al. (2003) supra; Drinane, et al. (2009) *Circ. Res.* 104(3):337-345; Moulton, et al. (1999) *Circulation* 99(13):1726-1732). Each of these inhibitors is a cleavage product of an extracellular matrix (ECM) protein (Mulligan-Kehoe, et al. (2002) *J. Biol. Chem.* 277(50):49077-49089; Mulligan-Kehoe, et al. (2001) *J. Biol. Chem.* 276(11):8588-8596; O'Reilly, et al. (1997) *Cell* 88(2):277-285; O'Reilly, et al. (1994) *Cell* 79(2):315-328).

The ECM and basement membrane (BM) provide a support scaffold that is essential for blood vessel stability. Adhesion of endothelial cells (EC) to the ECM enables them to undergo migration, proliferation and morphogenesis, which are all necessary for neovascularization (Rhodes & Simons (2007) *J. Cell Mol. Med.* 11(2):176-205). Degradation of the ECM/BM leads to vessel collapse/regression (Davis & Saunders (2006) *J. Investig. Dermatol. Symp. Proc.* 11(1):44-56; Davis & Senger (2005) *Circ. Res.* 97(11):1093-1107; Vernon &Sage (1995) *Am. J. Pathol.* 147(4):873-883). Proteases that degrade the ECM/BM play a key role in matrix remodeling during normal wound healing as well as in vascular diseases such as atherosclerosis (Garcia-Touchard, et al. (2005) *Arterioscler. Thromb. Vasc. Biol.* 25(6):1119-1127).

Plasmin contributes to matrix remodeling through its own proteolytic activity and by activating numerous matrix metalloproteinases (MMPs) (Garcia-Touchard, et al. (2005) supra; Bobik & Tkachuk (2003) *Curr. Hypertens. Rep.* 5(6): 466-472). Of those, MMP-1, -3, -9, -10 and -13 promote capillary network regression (Davis, et al. (2001) *J. Cell Sci.* 114(Pt 5):917-930; Saunders, et al. (2005) *J. Cell Sci.* 118(Pt 10):2325-2340). Plasmin also contributes to ECM remodeling by degrading fibrin (Vernon &Sage (1995) supra; Pepper (2001) *Arterioscler. Thromb. Vasc. Biol.* 21(7):1104-1117; Senger (1996) *Am. J. Pathol.* 149(1):1-7), an ECM protein that forms a supportive scaffold for angiogenic vessels (Dvorak, et al. (1992) *Ann. NY Acad. Sci.* 667:101-111; Nagy, et al. (1989) *Biochim. Biophys. Acta* 948(3):305-326. Fibrin, the major constituent of provisional matrix (Werb (1997) *Cell* 91(4):439-442), enables endothelial cells to adhere, spread and proliferate (Cheresh, et al. (1989) *Cell* 58(5):945-953; Suchiro, et al. (1997) *J. Biol. Chem.* 272(8):5360-5366). Fibrinogen extravasates from "leaky" angiogenic vessels, then accumulates in the matrix where it can be converted to fibrin by thrombin (Mosesson (2005) *J. Thromb. Haemost.* 3(8):1894-1904). Fibrin or accumulated fibrinogen can be broken down by plasmin to negatively regulate angiogenesis (Sahni & Francis (2003) *J. Thromb. Haemost.* 1(6):1271-1277). The breakdown products are released into the plasma. Plasmin also degrades nidogen (Mayer, et al. (1993) *Eur. J. Biochem.* 217(3):877-884) and perlecan (Whitelock, et al. (1996) *J. Biol. Chem.* 271(17):10079-10086), two of the four key components of the ECM/BM. Nidogen is a sulfated glycoprotein that connects two of the other key BM components, laminin and type IV collagen. Perlecan is a large heparan sulfate proteoglycan whose core protein binds many molecules to include nidogen, type IV collagen, laminin and angiogenic growth factors, FGF-2 and VEGF. Nidogen, perlecan, laminin and type IV collagen are important in blood vessel formation (Rhodes & Simons (2007) supra).

Plasminogen activator inhibitor-1 (PAI-1) is the primary inhibitor of plasmin production. It functions in this capacity by exposing a reactive center loop (RCL) that binds tissue plasminogen activator (tPA) or urokinase plasminogen activator (uPA). This interaction prevents the plasminogen activators from converting plasminogen to plasmin (Dellas & Loskutoff (2005) *Thromb. Haemost.* 93(4):631-640; Seiffert, et al. (1990) *Cell Differ. Dev.* 32(3):287-292).

It has been demonstrated that an anti-angiogenic truncated plasminogen activator inhibitor-1(PAI-1) protein, rPAI-1$_{23}$ (Mulligan-Kehoe, et al. (2002) supra; Mulligan-Kehoe, et al. (2001) supra; Drinane, et al. (2006) *J. Biol. Chem.* 281(44): 33336-33344), significantly inhibits angiogenesis in cultured endothelial cells and aortic rings from chick embryos by stimulating a high level of endothelial cell-specific apoptosis (Mulligan-Kehoe, et al. (2002) supra; Mulligan-Kehoe, et al. (2001) supra; Drinane, et al. (2006) supra). Additionally, rPAI-1$_{23}$ inhibits angiogenic vasa vasorum, reduces plaque area and plaque cholesterol in the descending aorta (DA) of hypercholesterolemic LDLR$^{-/-}$ ApoB48 deficient mice (Drinane, et al. (2009) supra). In this model, adventitial vasa vasorum in the saline-treated group have a lumen and form a defined vascular network, which is disordered, disrupted and appears to be collapsing in rPAI-1$_{23}$-treated mice.

SUMMARY OF THE INVENTION

The present invention provides methods for increasing plasmin activity, inhibiting angiogenic vasa vasorum, promoting plaque regression and treating atherosclerosis by administering to a subject in need of treatment an effective amount of recombinant plasminogen activator inhibitor type isoform 23 (rPAI-1$_{23}$). In some embodiments, rPAI-1$_{23}$ is set forth in SEQ ID NOs:5-8. In other embodiments, rPAI-1$_{23}$ is administered at a dose in the range of approximately 2.5 to 20 µg/kg/day. In further embodiments, the effective amount achieves a ratio of rPAI-1$_{23}$ to PAI-1 is in the range of approximately 1:2 to 3:1.

BRIEF DESCRIPTION OF THE DRAWINGS

FIG. 1A shows that plasmin production is increased when rPAI-1$_{23}$ is at the highest concentrations (FIG. 1A). As rPAI-1$_{23}$ concentrations decrease, plasmin activity declines in a stepwise manner (FIG. 1B).

FIG. 2A shows plasmin activity in reactions where rPAI-1$_{23}$ or PAI-1, at varied concentrations, were pre-bound to plasminogen in a 1 hour, 37° C. incubation before adding tPA for an additional 1 hour incubation. FIG. 2B shows plasmin activity in reactions where tPA, plasminogen, rPAI-1$_{23}$ or PAI-1 were added simultaneously to a reaction mixture and incubated at 37° C. for 1 hour. FIG. 2C shows plasmin activity in reactions where tPA, plasminogen, rPAI-1$_{23}$ and PAI-1 were added simultaneously to a reaction mixture and incubated for 1 hour at 37° C. Plasmin activity was measured in a chromozym assay. Data shown as mean±standard deviation and probability values were determined by ANOVA. *p≤0.05, **p≤0.001 vs. 90 nM rPAI-1$_{23}$.

DETAILED DESCRIPTION OF THE INVENTION

Figure 1A:
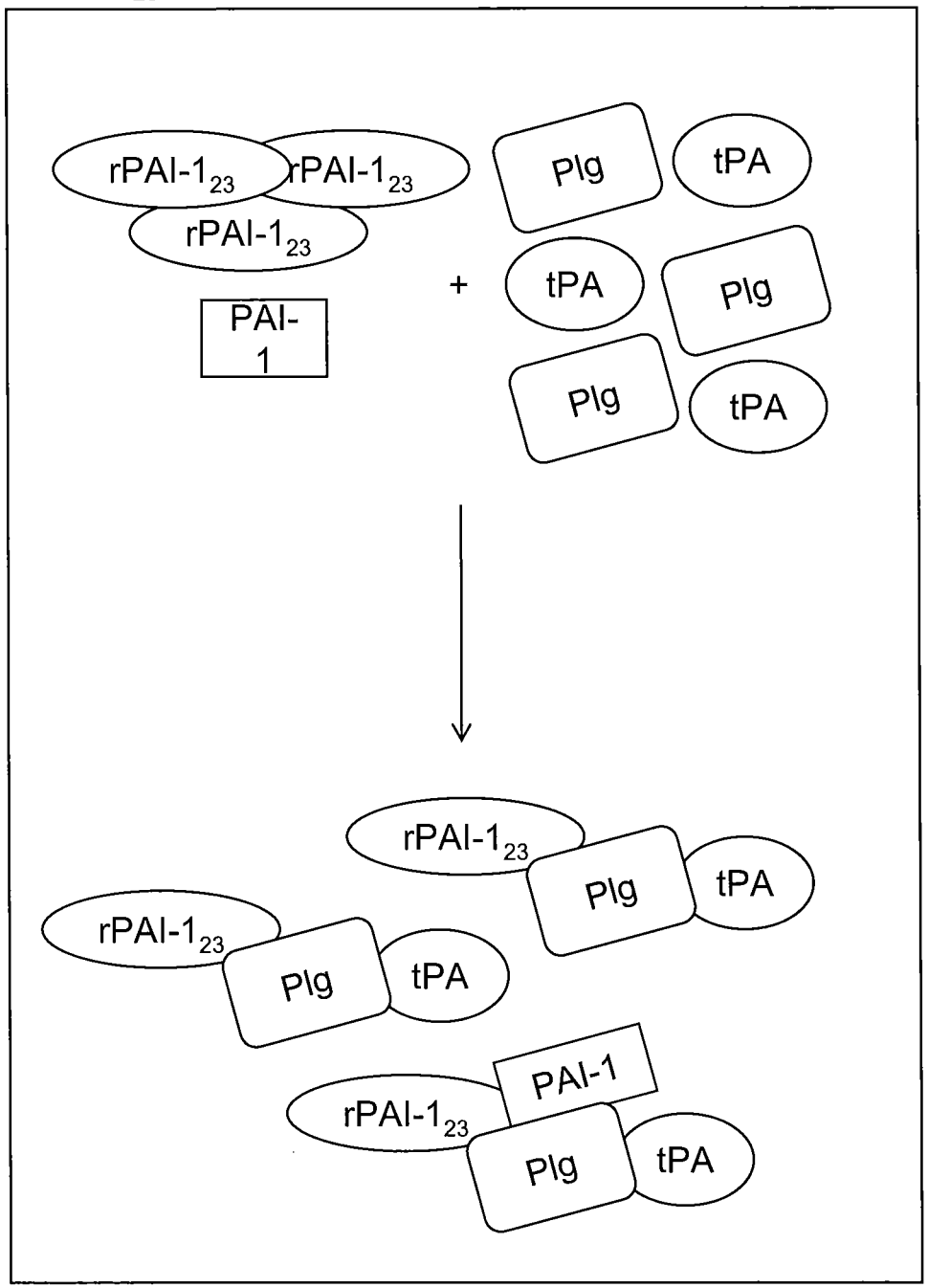
FIGS. 1A and 1B show the effects of simultaneously combining various concentrations of rPAI-1$_{23}$ and PAI-1 with plasminogen and tPA in a biochemical reaction.
Figure 1B:
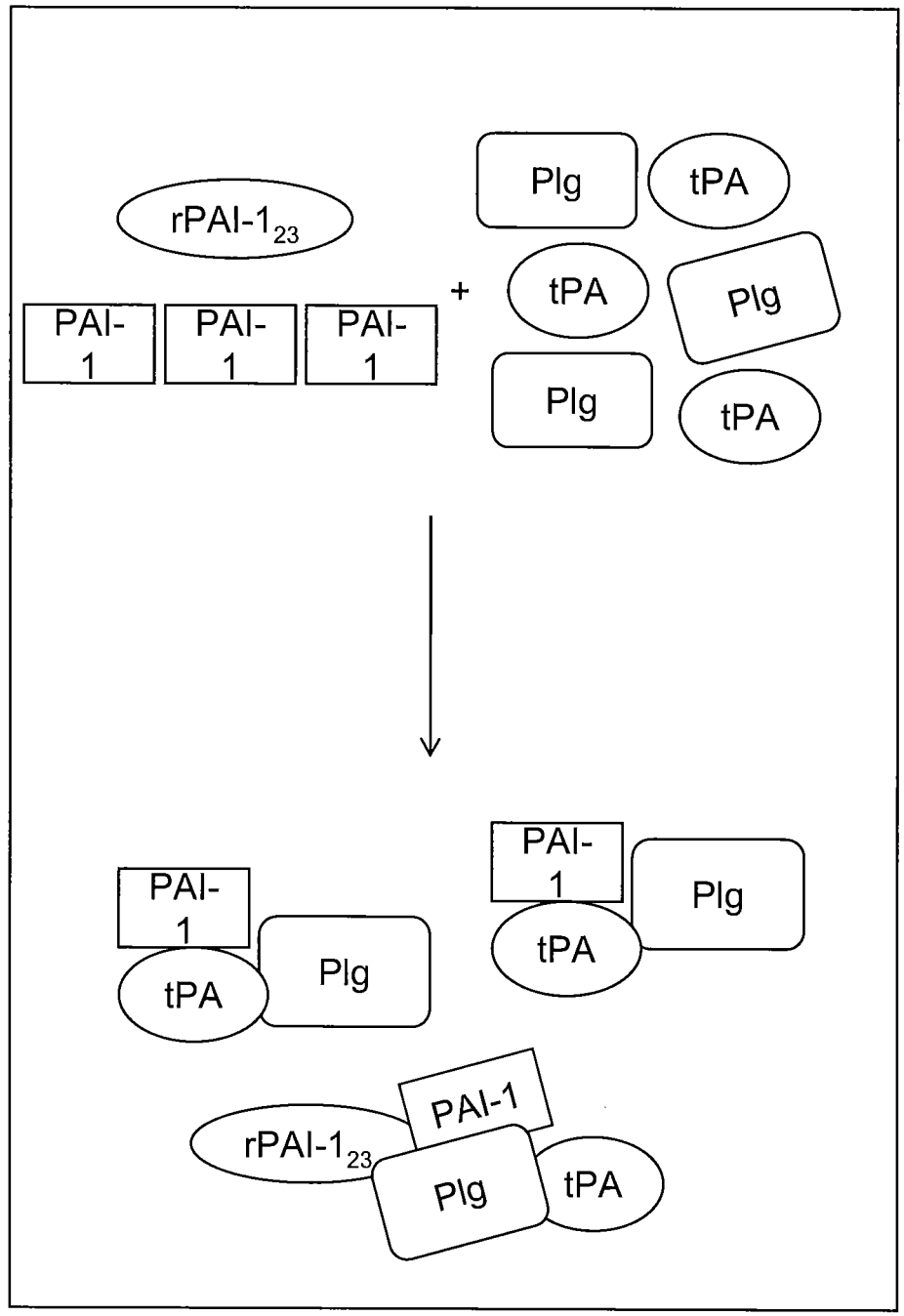

It has now been found that a potent anti-angiogenic protein, rPAI-1$_{23}$, causes regression/collapse of adventitial vasa vasorum in atherogenic female LDLR$^{-/-}$ApoB-48-deficient (DKO) mice by stimulating an increase in plasmin activity. The increased plasmin activity, accompanied by elevated MMP-3 activity, degrades major ECM/BM components that provide support to expanding vasa vasorum. Biochemical studies demonstrate that rPAI-1$_{23}$ enhanced plasmin activity is through a novel mechanism where rPAI-1$_{23}$ and PAI-1 bind plasminogen in a cooperative fashion to regulate plasmin activity. The effects of simultaneously combining various concentrations of rPAI-1$_{23}$ and PAI-1 with plasminogen and tPA favors plasmin production when rPAI-1$_{23}$ is at the highest concentrations (FIG. 1A). As rPAI-1$_{23}$ concentrations decrease, plasmin activity declines in a stepwise manner (FIG. 1B). Similarly, plasmin activity declines in a stepwise manner when rPAI-1$_{23}$ is in excess, but PAI-1 concentrations are reduced. These data indicate that rPAI-1$_{23}$ and PAI-1 work in a cooperative manner to regulate plasmin activity that is dependent upon the molar ratio of each relative to the other; the cooperativity requires the interaction of both molecules with plasminogen. The data indicate that rPAI-1$_{23}$ bound to plasminogen is the predominant interaction required for the conformational change in plasminogen. The data also indicate that PAI-1 has a greater affinity for the altered plasminogen conformation compared to its affinity for tPA; as more rPAI-1$_{23}$ molecules bind plasminogen to alter its conformation, then more PAI-1 molecules favor binding to plasminogen. Conversely, when rPAI-1$_{23}$ levels decline, there are more plasminogen molecules in a conformation that favors PAI-1 binding to tPA (FIG. 1B). Achieving levels of plasmin that exceed control levels, such as those measured in rPAI-1$_{23}$-treated hypercholesterolemic DKO mice, requires the high concentration of PAI-1. In light of this discovery, administration of rPAI-1$_{23}$ finds application in the treatment of atherosclerosis.

Accordingly, the present invention provides methods of increasing plasmin activity via recombinant PAI-1 isoform 23 (rPAI-1$_{23}$). rPAI-1$_{23}$ protein of use in the instant invention can be produced by any conventional methods (e.g., recombinant production, chemical synthesis or a combination thereof) and be derived from the sequence of any species. Indeed, there are no known functional differences between human (huPAI-1) and porcine PAI-1 (poPAI-1) (Bijnens, et al. ((1997) *Thromb. Haemost.* 77:350-356; Bosma, et al. (1988) *J. Biol. Chem.* 263:9129-9141). Exemplary PAI-1 and the rPAI-1$_{23}$ isoforms thereof are listed in Table 1.

TABLE 1

| | PAI-1 | | rPAI-1$_{23}$ |
|---|---|---|---|
| Species | Accession No. | SEQ ID NO: | SEQ ID NO: |
| Porcine | NP_999075 | 1 | 5 |
| Bovine | NP_776562 | 2 | 6 |
| Human | NP_000593 | 3 | 7 |
| Mouse | NP_032897 | 4 | 8 |

As is known in the art (see, e.g., Drinane, et al. (2006) *J. Biol. Chem.* 281:33336-33344) the rPAI-1$_{23}$ isoform of PAI-1 lacks an RCL domain and lacking a least a portion of the heparin-binding domain. Therefore, while specific rPAI-1$_{23}$ proteins are disclosed herein, it would be well within the ability of the skilled artisan, using the results provided by this disclosure, to generate additional rPAI-1$_{23}$ isoforms lacking at least a portion of the heparin-binding domain and lacking an RCL domain.

The rPAI-1$_{23}$ protein of the present invention may be purified from host cells that recombinantly express the same, in accordance with known techniques, or manufactured synthetically. Alternatively, the rPAI-1$_{23}$ protein may be used as part of a gene therapy approach. Recombinant rPAI-1$_{23}$ protein may be produced using methods exemplified herein or using other well-known methods for long-term, high-yield production of recombinant proteins. For example, nucleic acid sequences encoding, e.g., human, porcine, or bovine PAI-1$_{23}$, may be recombinantly engineered, using well-known methods, to produce the rPAI-1$_{23}$ protein of the present invention. A recombinant nucleic acid sequence encoding a rPAI-1$_{23}$ protein may then be incorporated into an expression vector. An expression vector is a replicable DNA construct in which a nucleic acid sequence encoding rPAI-1$_{23}$ protein is operably linked to suitable control sequences capable of effecting the expression of the isoform in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Vectors include plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites that are operably linked to the gene to be expressed and are operable in the host organism.

Suitable host cells include prokaryotes, yeast cells, or higher eukaryotic organism cells. Prokaryote host cells include gram negative or gram positive organisms, for example *Escherichia coli* (*E. coli*) or Bacilli. Higher eukaryotic cells include established cell lines of mammalian origin. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. See Bolivar, et al., ((1977) Gene 2:95). Promoters most commonly used in recombinant microbial expression vectors include the beta-lactamase (penicillinase) and lactose promoter systems (Chang, et al. (1978) *Nature* 275:615; Goeddel, et al. (1979) *Nature* 281:544), a tryptophan (trp) promoter system (Goeddel, et al. (1980) *Nucl. Acids Res.* 8:4057; EP36,776) and the tac promoter (De Boer, et al. (1983) *Proc. Natl. Acad. Sci. USA* 80:21). The promoter and Shine-Dalgarno sequence (for prokaryotic host expression) are operably linked to the DNA of the present invention, i.e., they are positioned so as to promote transcription of the messenger RNA from the DNA.

Eukaryotic microbes such as yeast cultures may also be used for recombinant expression. Yeast expression vectors generally contain an origin of replication from the micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb, et al. (1979) *Nature* 282:39; Kingsman, et al. (1979) *Gene* 7:141; Tschemper, et al. (1980) *Gene* 10:157). This plasmid contains the trp1 gene, which provides a selection marker for a mutant strain of yeast lacking the ability to grow in tryptophan, for example ATCC No. 44076 or PEP4-1 (Jones (1977) *Genetics* 85:12). The presence of the trp1 lesion in the yeast host cell genome then provides an effective environment for detecting transformation by growth in the absence of tryptophan.

Cultures of cells derived from multicellular organisms are also desirable hosts for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment that also contains the SV40 viral origin of replication. See Fiers, et al. (1978) *Nature* 273:113. Further, the protein promoter, control and/or signal sequences may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculorivus expression vector (e.g., vectors derived from *Autographa californica* MNPV, *Trichoplusia ni* MNPV, *Rachiplusia ou* MNPV, or *Galleria ou* MNPV) may be employed to make proteins useful in carrying out the present invention, as described in U.S. Pat. Nos. 4,745,051 and 4,879,236. In general, a baculovirus expression vector includes a baculovirus genome containing the gene to be expressed inserted into the polyhedrin gene at a position ranging from the polyhedrin transcriptional start signal to the ATG start site and under the transcriptional control of a baculovirus polyhedrin promoter.

In mammalian host cells, a number of viral-based expression systems can be used. In cases where an adenovirus is used as an expression vector, sequences encoding rPAI-1$_{23}$ can be ligated into an adenovirus transcription/translation complex composed of the late promoter and tripartite leader sequence. Insertion in a non-essential E1 or E3 region of the viral genome can be used to obtain a viable virus which is capable of expressing the PAI-1 or rPAI-1$_{23}$ protein in infected host cells (Logan and Shenk (1984) Proc. Natl. Acad. Sci. 81:3655-3659). In addition, transcription enhancers, such as the Rous sarcoma virus (RSV) enhancer, may be used to increase expression in mammalian host cells.

Rather than using vectors that contain viral origins of replication, one may transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival or transformants in culture medium that is toxic, or from which the cells cannot obtain critical nutrition without having taken up the marker protein.

Depending on the host cell to be transformed, any well-known means of introducing the expression vector containing nucleic acid sequences encoding rPAI-1$_{23}$ protein may be used. Following the introduction of the expression vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, et al. (1977) *Cell* 11:223-32) and adenine phospho-ribosyltransferase (Lowy, et al. (1980) *Cell* 22:817-23) genes which can be employed in tk- or aprt-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides neomycin and G-418 (Colbere-Garapin, et al (1981) *J. Mol. Biol.* 150:1-14) and als or pat, which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine (Hartman and Mulligan (1988) *Proc. Natl. Acad. Sci.* 85:8047-51). Alternatively, visible such as anthocyanins, β glucuronidase and its substrate GUS, and luciferase and its substrate luciferin, may be used not only to identify transformants, but also to quantify the amount of transient or stable protein expression attributable to a specific vector system (Rhodes, et al. (1995) *Methods Mol. Biol.* 55:121-131).

Host cells transformed with nucleotide sequences encoding rPAI-1$_{23}$ protein may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode rPAI-1$_{23}$ protein can be designed to contain signal sequences which direct secretion of the rPAI-1$_{23}$ protein through a prokaryotic or eukaryotic cell membrane. Other constructions may be used to join sequences encoding rPAI-1$_{23}$ protein to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the PAI-1 or rPAI-1$_{23}$ protein may be used to facilitate purification. One such expression vector provides for expression of a fusion protein containing rPAI-1$_{23}$ protein and a nucleic acid encoding six histidine residues preceding a thioredoxin or an enterokinase cleavage site. The histidine residues facilitate purification on IMAC (immobilized metal ion affinity chromatography) (see, e.g., Porath, et al. (1992) *Prot. Exp. Purif.* 3:263-281) while the enterokinase cleavage site provides a means for purifying the rPAI-1$_{23}$ protein from the fusion protein. A discussion of vectors which contain fusion proteins is provided in Kroll, et al. (1993) *DNA Cell Biol.* 12:441-453).

In addition to recombinant production of the rPAI-1$_{23}$ protein, the present invention also includes direct peptide synthesis using solid-phase techniques (Merrifield (1963) *J. Am. Chem. Soc.* 85:2149-2154). Protein synthesis can be performed using manual techniques or by automation. Automated synthesis may be achieved, for example, using Applied Biosystems 431A Peptide Synthesizer (Perkin Elmer). Various fragments of the rPAI-1$_{23}$ protein can be chemically-synthesized separately and combined using chemical methods to produce the full-length molecule.

Recombinant proteins provided herein may be used as isolated and substantially purified proteins in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the rPAI-1$_{23}$ protein may be incorporated into biodegradable polymers allowing for sustained release of the protein, the polymers being implanted in the vicinity of where drug delivery is desired, for example, at the site of a plaque so that the rPAI-1$_{23}$ protein is slowly released. Osmotic minipumps may also be used to provide controlled delivery of high concentrations of rPAI-1$_{23}$ protein through cannulae to the site of interest, such as directly into a metastatic growth or into the vascular supply to that tumor. The biodegradable polymers and their use are described, for example, in detail in Brem et al. ((1991) *J. Neurosurg.* 74:441-446).

The rPAI-1$_{23}$ protein formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

It is further contemplated that the rPAI-1$_{23}$ protein may be administered via cells which are genetically engineered to produce said proteins. In this respect, the rPAI-1$_{23}$ protein is not considered isolated and optionally purified.

The present invention provides administration of an "effective amount" of rPAI-1$_{23}$ proteins to increase plasmin activity, inhibit angiogenic vasa vasorum, promote plaque regression, disperse FGF-2, disorganize vessels, promote EC death and treat atherosclerosis. An "effective amount" is considered an amount of protein empirically determined to be necessary to achieve a reproducible change in plasmin activity or plaque regression (e.g., as determined by microscopic or macroscopic visualization) or in reducing the signs or symptoms of atherosclerosis as would be understood by one of ordinary skill in the art. In particular embodiments, an effective amount of rPAI-1$_{23}$ achieves a ratio of rPAI-1$_{23}$ to PAI-1 in the range of approximately 1:2 to 3:1. Ratios of rPAI-1$_{23}$ to PAI-1 can be determined by conventional methods of protein detection including, e.g., western blot analysis, and the like.

In some embodiments, a determination of whether the rPAI-1$_{23}$ protein is having the intended result is also included in the instant method. In this respect, the methods of the present invention further include the step of determining the activity of plasmin. Accordingly, administration of an effective amount of rPAI-1$_{23}$ yields a measurable increase (e.g., a 10%, 20%, 30%, 40%, 50%, or 60%) in the activity of plasmin as compared to a subject that has not received treatment with this protein. Desirably, the administration of an effective amount of rPAI-1$_{23}$ protein will also achieve at least a 40%, 50%, 60%, 70%, 80%, or more decrease plaque area as compared to plaques in a subject that has not received treatment with the rPAI-1$_{23}$ protein. As a consequence of increasing plasmin activity, inhibiting angiogenic vasa vasorum and promoting plaque regression, treatment of atherosclerosis will result in a lessening or amelioration of the symptoms of atherosclerosis. Such symptoms include, but are not limited to, artery blockage, shortness of breath, arrhythmias, fatigue, the inability to move limbs, dizziness, and pain.

The specific amount of rPAI-1$_{23}$ protein required by each individual will be dependent upon various factors. However, in particular embodiments of this invention, the rPAI-1$_{23}$ protein is administered at a dose in the range of approximately 2.5 µg/kg/day to 20 µg/kg/day or more particularly in the range of 5 µg/kg/day to 10 µg/kg/day. Given that the data herein indicate that rPAI-1$_{23}$ and PAI-1 work in a cooperative manner to regulate plasmin activity, which is dependent upon the molar ratio of each relative to the other, particular embodiments of the present invention include the administration of rPAI-1$_{23}$ to achieve a ratio of rPAI-1$_{23}$ to endogenous PAI-1 in the range of approximately 1:2 to 3:1. In some embodiments, the ratio of rPAI-1$_{23}$ to endogenous PAI-1 is approximately 1:2, 1:1, 2:1, or 3:1. Selection of the concentration of rPAI-1$_{23}$ and ratio of rPAI-1$_{23}$ to PAI-1 can be determined by the skilled clinician based upon the age, health, and weight of the recipient, kind of concurrent treatment, if any, frequency of treatment, and the nature of the effect desired.

The examples, which follow, are set forth to illustrate methods of the present invention, and are not to be construed as limiting thereof.

Example 1

Materials and Methods

Production of rPAI-1$_{23}$ Protein.

The rPAI-1$_{23}$ protein was produced and purified as previously described (Drinane, et al. (2006) supra). Briefly, the DNA encoding rPAI-1$_{23}$ protein was obtained by deleting the porcine PAI-1 gene (poPAI-1) (Mulligan-Kehoe, et al. (2002) supra; Mulligan-Kehoe, et al. (2001) supra; Bijnens, et al. (1997) *Thromb. Haemost.* 77(2):350-356). Selection of the gene fragment was based on the poPAI-1 sequences that correspond to the human PAI-1 gene (huPAI-1; Bosma, et al. (1988) *J. Biol. Chem.* 263(19):9129-9141) sequences reported to code for functional domains in human PAI-1. The DNA fragment was isolated from porcine aortic endothelial cells by reverse-transcribing RNA into cDNA. The cDNA was made double-stranded in a PCR reaction containing porcine PAI-1-specific primers (Mulligan-Kehoe, et al. (2002) supra; Mulligan-Kehoe, et al. (2001) supra). The PCR-amplified rPAI-1$_{23}$ DNA was ligated into a *Pichia pastoris* yeast shuttle vector, pGAPZ-α (Invitrogen, Carlsbad, Calif.). The TOP strain of *Escherichia coli* was transformed by electroporation. Positive isolates were verified by sequencing. The recombinant protein was expressed in *P. pastoris*. The secreted protein is purified on a heparin SEPHAROSE column containing 0.02% sodium azide. The rPAI-1$_{23}$ protein was eluted in 350-400 mM NaCl, and then dialyzed against PBS. The protein was tested at each purification step for potential bacterial, yeast and endotoxin contamination (Pyro-Gene recombinant Factor C endotoxin detection kit, Cambrex, Walkersville, Md.).

Mouse Strain, Diet and Treatment.

Female low-density lipoprotein receptor (LDLR)$^{-/-}$ apolipoprotein B (ApoB48)-deficient mice (DKO) (B6; 129S-Apob$^{tm2Sgy}$Ldlr$^{tm1Her}$/J) were purchased from Jackson Laboratory. Mice were fed either Paigen's diet without cholate (PD) or normal chow diet (CH) for 20 weeks and received either rPAI-1$_{23}$ (5.4 μg/kg/day) or saline treatment for the last six weeks of the diet, as previously described (Drinane, et al. (2009) supra). Briefly, twelve week old, weight-matched female LDLR$^{-/-}$ ApoB48-deficient mice were fed Paigen's atherogenic diet (Paigen, et al. (1985) *Atherosclerosis* 57(1):65-73) without cholate (PD) for a total of 20 weeks. One group received intraperitoneal injections of rPAI-1$_{23}$ (5.4 μg/kg/day) beginning at week 14 of PD and another group received saline treatment. The rPAI-1$_{23}$ dose was based on in vivo MATRIGEL plug assays in C57B6 mice.

LDLR$^{-/-}$ApoB100$^{+}$/PAI-1$^{-/-}$ mouse strain (DKO/PAI-1$^{-/-}$) were produced by crossing B6; 129S-Apobtm2Sgy Ldlrtm1Her/J/ with B6.129S2-Serpine1$^{tm1M1g}$/J (Jackson Laboratory, stock 002507). They were backcrossed for a minimum of 7 generations.

A soluble FGFR1 produced in an adenoviral construct (sFGFR1) (Murakami, et al. (2008) *J. Clin. Invest.* 118:335-3366). The construct was delivered by intraperitoneal injection to DKO mice at 14 weeks of PD. Mice were perfused and euthanized 10 days post delivery.

Animal care and procedures were performed in accordance with the guidelines of the Animal Care and Use Committee and procedures outlined in the *Guide for the Care and Use of Laboratory Animals* (NIH publication No. 86-23, 1985). All procedures were approved by Dartmouth College.

Perfusion.

Mice were injected with 50 μl of heparin. After 10 minutes the mice were given an injection of 0.1 ml ketamine per 30 grams of weight. The mice were euthanized, perfused with phosphate-buffered saline (PBS) followed by 3.5% paraformaldehyde (PFA) under 110-120 mm/Hg pressure. Alternatively, mice were perfused with PBS followed by: (1) PBS containing 1% bovine serum albumin (BSA) and 1% fluorescein-labeled *Lycopersicon esculentum* lectin (FITC-lectin) (Vector Laboratories, Burlingame, Calif.); (2) PBS containing 1% bovine serum albumin (BSA); (3) PBS containing calcium, magnesium, 1% BSA, 2% glutaraldehyde, 1% PFA. N=17/group.

Zymographic Detection of Proteolytic Activity in Mouse Plasma.

Blood from fasted LDLR$^{-/-}$ApoB48-deficient mice treated with either rPAI-1$_{23}$ or saline, as previously described (Drinane, et al. (2009) supra), was collected into either sodium citrate or lithium heparin tubes (Thermo Scientific, Pittsburgh, Pa.). Plasma was separated by centrifugation. Equivalent amounts of plasma protein were resolved on a casein zymogram (Mulligan-Kehoe, et al. (2002) supra; Mulligan-Kehoe, et al. (2001) supra) or on a polyacrylamide gel containing 1 mg/ml of gelatin. Detection of proteolytic and gelatinolytic proteins were as previously described for casein zymograms (Mulligan-Kehoe, et al. (2002) supra; Mulligan-Kehoe, et al. (2001) supra).

Plasmin Activity Measurement.

Plasmin activity, in 168 μg of plasma protein (sodium citrated collected) from rPAI-1$_{23}$- and saline-treated hypercholesterolemic mice, was measured in a fluorometric mouse plasmin activity assay kit (Molecular Innovations, Novi, Mich.) and in a chromozym PL assay (Roche, Indianapolis, Ind.) with and without active alpha 2 antiplasmin (3.2 μg/well) (Abcam, Cambridge, Mass.) and aprotinin (10 μg/well) (Roche). The assay was performed according to the manufacturer's instructions. Each plasma sample was measured in triplicate wells and the experiment was performed twice in n=6 per group. Control wells for each sample included all assay components except the substrate or chromozym. Activity was calculated based on the manufacturer's formula after protein background and residual inhibitor readings were subtracted.

Measurement of MMP Activity.

MMP-3 activity in 600 μg of mouse plasma protein collected into lithium heparin tubes was measured with and without 3.2 μM N-[[(4,5-dihydro-5-thioxo-1,3,4-thiadiazol-2-yl]carbonyl]-L-phenylalanine, an MMP-3-specific inhibitor (EMD Biosciences, Gibbstown, N.J.), in a fluorometric assay kit according to the manufacturer's instructions (ENZO Life Sciences, Plymouth Meeting, Pa.). Each plasma sample (n=9 for rPAI-1$_{23}$, n=7 for saline) was measured in triplicate wells and the experiment was performed twice. Control wells for each sample included all assay components except the substrate. Activity was calculated based on the manufacturer's formula after protein background and residual inhibitor readings were subtracted.

Western Blot Analysis of Fibrinogen.

Equivalent amounts of either adventitial or plasma protein from saline- and rPAI-1$_{23}$-treated mice were gel-resolved and transferred to nitrocellulose. The membrane was probed for fibrin(ogen) (Dako, Carpinteria, Calif.) on a western blot. Equivalent amounts of either descending aorta or plasma protein from saline- and rPAI-1$_{23}$-treated mice were gel-resolved and transferred to nitrocellulose. The membrane was probed for fibrin(ogen) (Dako, Carpinteria, Calif.) in an overnight incubation at 4° C. The binding reaction was amplified in a 1 hour room temperature incubation with horseradish peroxidase-conjugated donkey anti-rabbit secondary antibody (Drinane, et al. (2006) supra). The binding reaction was detected with SUPERSIGNAL West Pico chemiluminescent substrate (Thermo Scientific, Rockford, Ill.). Similarly, adventitial protein was probed for fibrin(ogen) following the same protocol. Antibodies do not differentiate between fibrinogen and fibrin, therefore they are denoted as fibrin (ogen).

D-Dimer Assay.

Equivalent amounts of plasma protein (sodium citrated collected), from hypercholestrolemic mice treated with either rPAI-1$_{23}$ or saline, were analyzed for fibrin(ogen) breakdown products in a quantitative D-dimer Elisa kit, according to the manufacturer's instructions (Diagnostica Stago, Parsippany, N.J.). N=5 per group.

Immunohistochemical Analysis of Fibrin(ogen).

Ten micron frozen sections of the descending aorta (DA) from untreated and rPAI-1$_{23}$-treated hypercholestrolemic mice were probed for fibrin(ogen) with a rabbit anti-human polyclonal primary antibody (Dako). The binding reaction was detected with a horseradish peroxidase-conjugated secondary antibody (GE Healthcare, Piscataway, N.J.) as previously described (Drinane, et al. (2009) supra). Briefly, ten micron frozen sections of the descending aorta were probed for fibrin(ogen) with a rabbit anti-human polyclonal primary antibody (Dako) in a 4° C. overnight incubation. A horseradish peroxidase-conjugated donkey anti-rabbit secondary antibody (Amersham) amplified the binding reaction in a 2 hour room temperature incubation. The enzymatic reaction was detected with DAB chromagen (BD Pharmingen). N=6 mice per treatment group.

Confocal Imaging of Nidogen-Probed Basement Membrane.

Hypercholesterolemic mice from each treatment group were perfused with fluorescein-labeled *Lycopersicon esculentum* lectin (FITC-lectin). The adventitia was probed for nidogen (Millipore, Billerica, Mass.). Adventitial basement membrane stability in DA whole mounts was examined by confocal microscopy at 20 and 63× magnification as previously described (Drinane, et al. (2009) supra). Briefly, atherogenic mice from each treatment group were perfused with fluorescein-labeled *Lycopersicon esculentum* lectin (FITC-lectin). Adventitial basement membrane stability in DA whole mounts was examined by confocal microscopy (Drinane, et al. (2009) supra). The adventitia was probed for nidogen, a basement membrane marker (Millipore, Billerica, Mass.) in an overnight reaction at 4° C. A goat anti-rat secondary antibody conjugated to ALEXA 568 (Molecular Probes Invitrogen, Carlsbad, Calif.) amplified and detected the binding reaction. Z-stack images were acquired on a ZEISS LSM-510 META point scanning confocal microscope (Thornwood, N.Y.). N=4 per group.

Confocal Imaging of Vasa Vasorum and FGF-2 in Descending Aorta Whole Mounts.

Mice were perfused with FITC-lectin. The descending aorta (DA) to the iliac bifurcation was surgically removed and probed for FGF-2 (Sigma, St. Louis, Mo.). DA whole mounts were examined by confocal microscopy at 20 and 63× magnification and z-stacks were collected as previously described (Drinane, et al. (2009) *Circ. Res.* 104:337-345). N=8/group.

Quantification of Confocal Images.

Confocal z-stack slices were aligned in volumetric images. The resolution of the reconstructed volumetric data was increased by tri-linear interpolation for a detailed geometrical representation in 3-D. MICROVIEW software (GE Healthcare, Piscataway, N.J.) was used to quantify the volume and area of FGF-2 and lectin. Quantitative values were obtained from the program generated isosurface. The two images were overlaid. N=4/group.

Detection of FGF-2, Perlecan and CD31 in the Adventitia of Descending Aortas.

Sequential 10-15 micron frozen sections of DA from rPAI-1$_{23}$- and saline-treated PD DKO mice were incubated with saline, plasmin (139 nM) (Molecular innovations), APMA-activated MMP-3 (185 nM) (EMD Biosciences) or plasmin+MMP-3 in a 15 hour, 37° C. incubation. Next the sections were incubated overnight at 4° C. with an antibody specific for perlecan (Santa Cruz, Santa Cruz, Calif.). The detection of FGF-2 Confocal images at 63× magnification were acquired.

Quantitative Analysis of Plasminogen Activator Activities and Expression Levels.

tPA and uPA activities in 160 µg of plasma protein collected in sodium citrate tubes were measured in chromozym activity assays (Roche). Protein expression levels were determined by ELISA in 600 µg of plasma protein (American Diagnostica, Stamford, Conn.). The experiments were performed in triplicate wells per sample (N=8 per test group) according to the manufacturer's instructions.

PAI-1 Activity Measurements.

PAI-1 activity was measured in equivalent amounts of plasma protein (600 µg) isolated from rPAI-1$_{23}$— or saline-treated mice using two methods. One method measured activity by ELISA (AssayPro, St. Charles, Mo.) and the other in a chromogenic assay (American Diagnostica). The experiment was performed on plasma collected into sodium citrate tubes from 5 mice per treatment group following the manufacturers' protocol. Each assay was repeated twice in triplicate wells per sample. N=5 per group.

Measurement of PAI-1 Protein Expression.

PAI-1 protein in 600 µg of mouse plasma (sodium citrated collected) was measured in a mouse PAI-1 total antigen kit (Molecular Innovations) according to the manufacturer's instructions. The experiment was performed twice in triplicate wells per sample (N=8 per test group). Control wells for each sample included all assay components except the detection substrate.

Measurement of Plasminogen Protein Expression.

Equivalent amounts (600 µg) of plasma protein (sodium citrated collected) from hypercholesterolemic rPAI-1$_{23}$— or saline-treated mice were assayed for plasminogen expression levels using a mouse plasminogen ELISA kit (Molecular Innovations). The experiment was performed according to the manufacturer's instructions. Each sample was tested in triplicate in N=8 per group.

Plasmin Activity Measurement.

Plasmin activity, in 168 μg of plasma protein (sodium citrated-collected) was measured in a chromozym PL assay (Roche, Indianapolis, Ind.). N=6/group Detection of PAI-1 in Descending Aorta Protein.

The thoracic DA was removed from hypercholesterolemic, female $LDLR^{-/-}ApoB48$-deficient mice treated with rPAI-$1_{23}$ or saline. Equivalent amounts of pooled protein from five mice per group were probed for PAI-1 on a western blot using a monoclonal antibody that has affinity for latent and active forms of PAI-1 (EMD Biosciences). Glyceraldehyde 3-phosphate dehydrogenase (GAPDH) (Fitzgerald Industries International, Concord, Mass.) was used as a lane loading control.

Co-immunoprecipitation of rPAI-$1_{23}$ and PAI-1 with Plasminogen. Equivalent amounts (320 μg) of pooled protein, isolated from the thoracic DA from five hypercholesterolemic mice treated with either rPAI-$1_{23}$ or saline, were incubated overnight at 4° C. with 1 μg of a monoclonal antibody to active and latent forms of PAI-1 (EMD Biosciences). The antibody●PAI-1 complexes were incubated with protein G-coupled magnetic beads for 1 hour at room temperature. Unbound proteins were removed by applying a magnetic strip to the samples. Equal volume of protein G-bound anti-PAI-1●PAI-1 complexes were probed with an antibody specific for plasminogen kringles 1-3 domain (EMD Biosciences) on western blots. The binding reaction was amplified and detected using known methods (Mulligan-Kehoe, et al. (2007) *Arthritis Rheum.* 56(10):3448-3458). The membrane was cut above 80 kD and probed with a secondary antibody to PAI-1 to determine lane loading.

Binding Affinity Assays.

An antibody specific for plasminogen kringles 5+ the serine protease domain (American Diagnostica) was bound to protein G-coupled magnetic beads. One microgram of PAI-1 and rPAI-$1_{23}$ were biotinylated using EZ-Link Amine-PEGn-biotin (Thermo Scientific). Each biotinylated protein was incubated with 1.8 micrograms Lys-plasminogen (EMD Biosciences) for 1 hour at room temperature followed by a second 1 hour, room temperature incubation with the antibody●protein G●bead complex. The final biotinylated rPAI-$1_{23}$ (or PAI-1)●plasminogen●antibody●protein G●bead complex was isolated with a magnet and washed exhaustively to remove unbound molecules. A 1:2000 dilution of horseradish peroxidase-conjugated streptavidin-HRP (Thermo Scientific) was added to the bead-bound complex and incubated at room temperature for 1 hour. The final complex was isolated with a magnet, washed exhaustively, then incubated for 1 hour at room temperature with either PAI-1 or rPAI-$1_{23}$ at concentrations ranging from 0-0.5 μg. Following the incubation, the magnetic bead-bound complex was isolated by magnet; the unbound liquid fraction was saved. The bound and unbound fractions were incubated with 3,3',5,5'-tetramethylbenzidine substrate (TMB) (Thermo Scientific) for 5 minutes before obtaining colorimetric change at 370 nm on a spectrophotometer (Bio TEK, Winooski, Vt.). Readings were obtained every 2 minutes until saturation was reached.

Biochemical Analysis of rPAI-$1_{23}$ Modulation of Plasmin Activity.

Biochemical reactions containing tPA (American Diagnostica) and plasminogen (Molecular Innovations) were incubated for 1 hour with either 25, 50 or 90 nM rPAI-$1_{23}$, 12, 25 or 50 nM glycosylated human PAI-1 (Molecular Innovations) or combinations of the two. In a second set of reactions, tPA was added at two different time points: (a) simultaneously with plasminogen, PAI-1 and/or rPAI-$1_{23}$; or (b) following a 1 hour, 37° C. incubation of reactions containing plasminogen, rPAI-$1_{23}$ and/or PAI-1. A 1 hour incubation at 37° C. followed the addition of tPA. Plasmin activity was measured in a plasmin chromozym assay (Roche) in triplicate wells in three separate experiments. The three sets of experiments were normalized to the tPA+plasminogen controls.

Measurement of rPAI-$1_{23}$-Stimulated Proteolytic Activity in Endothelial Cells.

Human umbilical vein endothelial cells (HUVECs) were grown in medium supplemented with 10% fetal bovine serum. Cells were incubated for 18 hours at 37° C. with rPAI-$1_{23}$ (90 nM), PAI-1 (50 nM), or rPAI-$1_{23}$+PAI-1. Each culture was supplemented with 2 nM plasminogen. Untreated HUVECs served as the control. Culture medium was collected after 18 hours of incubation. Plasmin, MMP-3 and PAI activities, with and without their respective inhibitors, were measured in conditioned medium. N=3 per group.

Detection of Endothelial Cell Death in the Vasa Vasorum.

Propidium iodide (20 mg/kg) (Sigma) was injected intraorbitally in 4 increments over a period of 15 minutes. Mice were perfused and euthanaized 20 minutes after the final injection. N=3/group.

Endothelial Cell Tube Formation in a Collagen Overlay Assay.

Angiogenesis was stimulated by adding fibroblast growth factor (FGF-2) (25 ng/ml)(EMD Biosciences) to the conditioned medium collected from HUVECs treated with rPAI-$1_{23}$, PAI-1, or rPAI-$1_{23}$+PAI-1 for 18 hours. The mixture was added to HUVECs embedded in a collagen-1 overlay. Complete endothelial cell enclosures were counted in five fields per three wells after 18 hours of incubation at 37° C., as previously described (Drinane, et al. (2006) supra; Mulligan-Kehoe, et al. (2007) supra).

Statistical Analysis.

Statistical analysis was performed with a two-tailed indirect Student's t-test, one way analysis of variance (ANOVA) with a post-hoc least significant difference (LSD) test with or without repeated measures or with a chi square test, as appropriate, using the SPSS 12.0.1 statistical software package.

Example 2 rPAI-$1_{23}$ Treatment Increases Proteolytic Activity in Plasma from Hypercholesterolemic Mice The rPAI-$1_{23}$ protein lacks the RCL that contains the binding site for tPA and uPA; therefore, it was contemplated that plasmin activity may be altered in hypercholesterolemic (PD) $LDLR^{-/-}ApoB48$-deficient (DKO) mice treated with rPAI-$1_{23}$. Proteolysis examined by casein zymography in hypercholesterolemic (PD) mice treated with rPAI-$1_{23}$ or saline or untreated, non-hypercholesterolemic mice (CH) suggested that plasma from rPAI-$1_{23}$-treated mice had more plasmin activity when compared to the saline and untreated controls. A plasmin chromogenic assay measured 1.6-fold more plasmin activity in PD, rPAI-$1_{23}$-treated DKO mice compared to the PD, saline control (rPAI-$1_{23}$, $0.8 \times 10^{-3} \pm 0.07 \times 10^{-3}$ vs. saline, $0.5 \times 10^{-3} \pm 0.1 \times 10^{-3}$ U/ml; p=0.04). Non-hypercholesterolemic (CH) DKO mice treated with rPAI-$1_{23}$ were not significantly greater than the CH controls. Plasmin inhibitors, alpha 2 antiplasmin and aprotinin, blocked plasmin activity in all conditions. An active plasmin capture immunoassay measured similar differences in the concentration of active plasmin in PD rPAI-$1_{23}$-treated mice compared to the saline counterpart (rPAI-$1_{23}$, 5.6±0.54 vs. saline 3.7±0.57 ng/ml, p=0.03).

Plasmin activates numerous MMPs, therefore, potential plasmin activity effects on MMP activity in plasma from PD rPAI-$1_{23}$, PD saline and untreated CH mice were examined on gelatin zymograms. The rPAI-1$_{23}$-treated mice have significantly more gelatinolytic activity when compared to the two control groups. An activity assay for MMP-3 measured 1.3-fold more hydrolyzed MMP-3 substrate in the PD rPAI-1$_{23}$-treated mice compared to the saline counterpart (rPAI-1$_{23}$, 23±0.6 vs. saline, 18±0.45 pmoles substrate hydrolyzed/minute, p<0.001) and 1.2-fold more than the CH rPAI-1$_{23}$-treated DKO mice (CH rPAI-1$_{23}$,19±2 pmoles substrate hydrolyzed/minute, p=0.04). An MMP-3 inhibitor blocked 90% of the activity. Assays for MMP-9 showed residual activity and no differences were measured in MMP-2 and MMP-10 activities. This set of experiments clearly demonstrates that rPAI-1$_{23}$ activity significantly increases proteolytic activities in PD DKO mice compared to the saline counterpart.

Example 3 rPAI-1$_{23}$ Generates Fibrin(ogen) Breakdown Products

Plasmin activity was further validated by examining fibrin(ogen) breakdown in plasma from the PD treatment groups. Equivalent amounts of plasma protein probed for fibrin(ogen) on western blots showed distinct differences in the pattern of fibrin(ogen) breakdown products between the two treatment groups. Plasma from most saline-treated mice contained a defined fragment at 115 kD, while plasma from the rPAI-1$_{23}$-treated mice was degraded to a smaller fragment near 50 kD. Protein isolated from the DA within the thoracic cavity of each treatment group was pooled and probed for fibrin(ogen). Western blots showed that fibrin(ogen) degradation products in the DA from rPAI-1$_{23}$ mice were substantially greater than the saline control.

D-dimer assays measured 1.65-fold more fibrin(ogen) breakdown products in the plasma from the rPAI-1$_{23}$ treatment group when compared to the control (rPAI-1$_{23}$, 229±25 vs. saline, 139±20 ng/ml, p=0.001); thus adding quantitative evidence for loss of fibrin(ogen) stability in rPAI-1$_{23}$-treated mice.

The effect of rPAI-1$_{23}$-stimulated proteolysis on fibrin(ogen) in plaque and the ECM supporting the DA wall was examined by probing DA cross sections for fibrin(ogen). The overall expression of fibrin(ogen) in the ECM and adjacent plaque was barely detectable in rPAI-1$_{23}$-treated mice, while the saline-treated mice had extensive levels of fibrin(ogen) in both areas. Fibrin(ogen) observed in the ECM of saline-treated mice followed a distinct structural pattern that was absent in rPAI-1$_{23}$-treated mice. Plaque fibrin(ogen) was barely detectable in rPAI-1$_{23}$-treated mice, while plaque from the saline group contained large areas of dense fibrin(ogen). The combined data from these experiments provided evidence of proteolytic degradation of fibrin(ogen).

Example 4

Basement Membrane Breakdown in rPAI-1$_{23}$-Treated Mice

The effects of rPAI-1$_{23}$-enhanced proteolytic activity on basement membrane (BM) stability were examined in the adventitia of rPAI-1$_{23}$- and saline-treated PD mice. The adventitia of DA whole mounts from mice perfused with FITC-labeled lectin was probed for nidogen, a BM marker that is proteolytically cleaved by plasmin (Mayer, et al. (1993) supra). Images acquired by confocal microscopy at 20× and 63× magnification showed that the saline-treated mice had an organized vasa vasorum network that was extensively co-localized with nidogen. On the other hand, the adventitia of rPAI-1$_{23}$-treated mice had very low levels of nidogen expression, the lectin-perfused vessels were discontinuous, collapsing and demonstrated loss of the vascular network.

Further examination of rPAI-1$_{23}$-stimulated effects on ECM/BM breakdown was performed on DA cross sections from saline- and rPAI-1$_{23}$-treated PD mice. Sequential sections were incubated with plasmin, MMP-3 or both. Next, the sections were probed for the perlecan core protein, which is reported to be degraded by plasmin and MMP-3 (Whitelock, et al. (1996) supra). Confocal images of the perlecan-probed sections from rPAI-1$_{23}$-treated mice lacked perlecan in the matrix surrounding the DA and CD-31-probed vessels lacked an organized structure. On the other hand, sections from the saline-treated mice had a distinct distribution of perlecan that was co-localized with vascular structures. Sequential sections from the saline-treated mice that were incubated with plasmin had a significant loss of perlecan, which was completely absent following exposure to plasmin and MMP-3.

Taken together, these data show that the ECM/BM surrounding the DA of rPAI-1$_{23}$-treated hypercholesterolemic DKO mice undergo a degradative process that impacts the stability of the adventitial vessels. This process is partially due to the combined proteolytic activities of plasmin and MMP-3.

Example 5

Plasminogen, tPA and uPA Expression and Activity Levels are not Altered by rPAI-1$_{23}$ It was subsequently examined whether elevated protein expression and/or activity levels of plasminogen, tPA or uPA in rPAI-1$_{23}$-treated mice could explain the higher plasmin activity. Plasminogen expression levels measured in PD rPAI-1$_{23}$- and saline-treated mice were very similar (rPAI-1$_{23}$, 0.11±0.03 vs. saline, 0.13±0.04 ng/ml, p=NS). A tPA chromozym activity assay did not show significant differences in PD mice treated with rPAI-1$_{23}$, saline or untreated CH mice (rPAI-1$_{23}$ 1.8±0.5, saline 1.8±0.2, CH 1.3±0.06 units/ml, p=NS). Similarly, ELISA assays did not detect differences in tPA protein expression (rPAI-1$_{23}$ 1.5±0.14 vs. saline 1.6±0.17 ng/ml, p=NS). Urokinase activities and protein expression levels were below the lower limits of detection.

Example 6

Reduced PAI-1 Activity in rPAI-1$_{23}$-Treated Hypercholesterolemic Mice

Since PAI-1 is the primary inhibitor of tPA/uPA conversion of plasminogen to plasmin, its activity was measured in equivalent amounts of plasma protein from rPAI-1$_{23}$- and saline-treated PD mice. The rPAI-1$_{23}$-treated mice had a significant 48% reduction in PAI-1 activity compared to the saline counterpart (rPAI-1$_{23}$, 8.5+3.5 vs. saline, 20.4+2.6 U/ml, p=0.001). PAI-1 activity in the rPAI-1$_{23}$-treated mice was comparable to that measured in untreated, CH mice (untreated, CH, 8.25+3.5 IU/ml).

PAI-1 protein expression levels measured in an ELISA assay did not show a significant difference between rPAI-1$_{23}$- and saline-treated PD mice (rPAI-1$_{23}$, 0.49±0.04 vs. saline, 0.41±0.04, p=NS). Furthermore, the concentration of PAI-1 in the two treatment groups was significantly higher than the untreated CH control (untreated CH 0.18±0.03, P<0.001).

Example 7

PAI-1 is Complexed with Plasminogen in the Descending Aorta

A potential explanation for reduced PAI-1 activity in rPAI-$1_{23}$-treated mice is that PAI-1 may be degraded at a faster rate. Equivalent amounts of pooled protein isolated from DA of rPAI-$1_{23}$- or saline-treated PD mice were probed for PAI-1 on a western blot. PAI-1 at 50 kD and potential cleavage/degradation products were not detected in the protein from rPAI-$1_{23}$-treated mice, but PAI-1 was found at a molecular mass near 80 kD. The protein from saline-treated mice contained PAI-1 at 50 kD, 80 kD and smaller fragments ranging from 30-45 kD. These data indicated that PAI-1 at 80 kD was complexed with another protein. That possibility was investigated by immunoprecipitating PAI-1 from the pooled DA protein with an antibody that had affinity for active and inactive PAI-1. The antibody-bound complexes were probed for plasminogen kringles 1-3 on a western blot. Plasminogen was detected in the PAI-1 antibody-precipitated protein complex from both rPAI-$1_{23}$— and saline-treated mice. However, densitometry measurements indicated that there was 1.6-fold more plasminogen complexed with PAI-1 in the descending aorta of rPAI-$1_{23}$-treated mice. These data showed that PAI-1 and plasminogen form a complex with each other, a finding no previously shown. Additionally, it indicates that the interaction modulates PAI-1 activity and subsequent plasmin levels.

Example 8 rPAI-$1_{23}$ and PAI-1 Bind Plasminogen

An immunoprecipitation reaction containing purified plasminogen and PAI-1 validated that PAI-1 binds plasminogen. The immunoprecipitation assay was repeated in reactions containing plasminogen, tPA, PAI-1 and/or rPAI-$1_{23}$ to determine if tPA or rPAI-$1_{23}$ altered the ability of PAI-1 to bind plasminogen. PAI-1 antibody-precipitated complexes probed for plasminogen kringles 1-3 showed that plasminogen formed a complex with PAI-1, rPAI-$1_{23}$ or a mixture of both isoforms in the presence of tPA. Binding affinity studies showed that rPAI-$1_{23}$ had slightly less affinity for plasminogen compared to PAI-1 (Kd rPAI-$1_{23}$, 31.1×10$^{-9}$ vs. Kd PAI-1, 8.1×10$^{-9}$).

Example 9 rPAI-$1_{23}$ Enhances Plasmin Activity in Biochemical Reactions

Figure 2A:
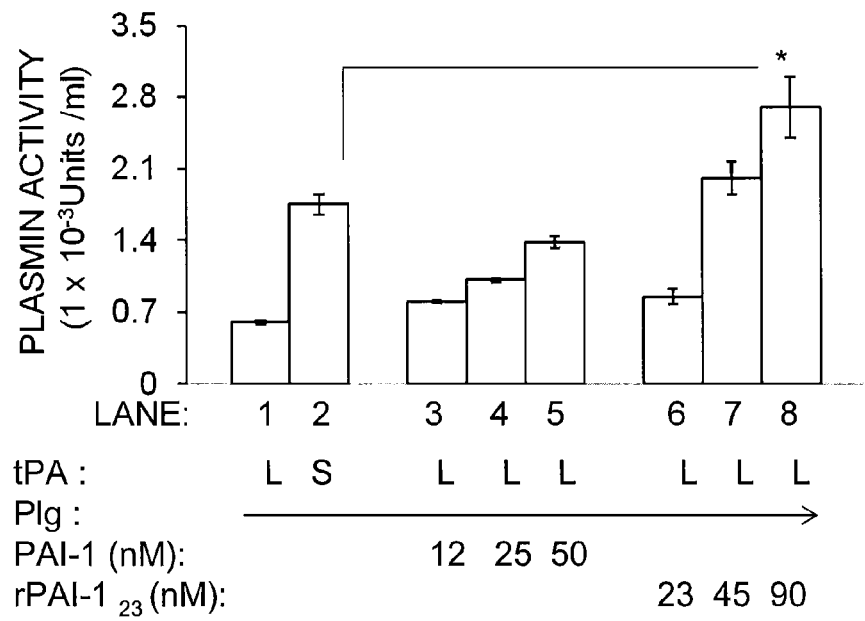
FIGS. 2A-2C show plasmin activity in biochemical reactions containing plasminogen, tPA, rPAI-1$_{23}$ and/or PAI-1. Biochemical reactions containing plasminogen, tPA, rPAI-1$_{23}$ and/or PAI-1 were performed under varied conditions.
Figure 2B:
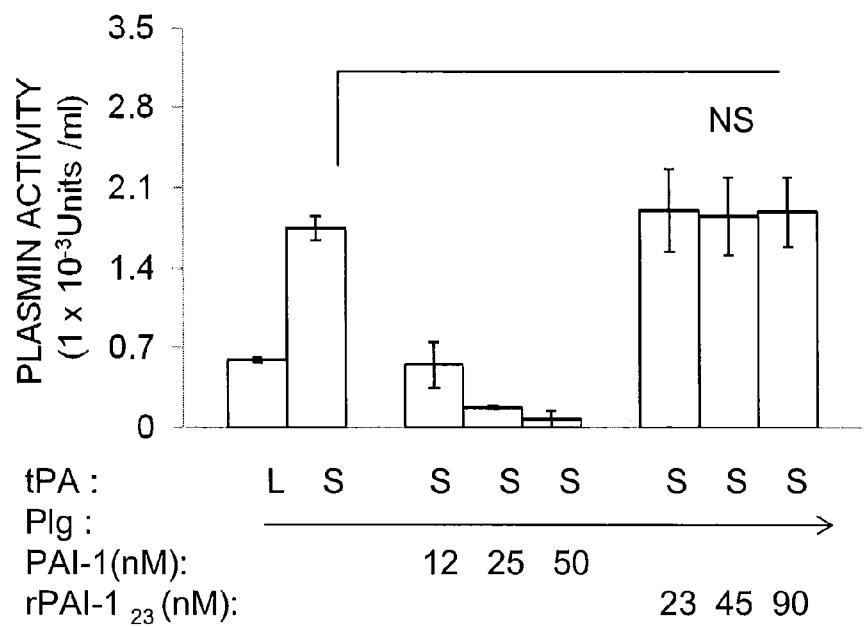
Figure 2C:
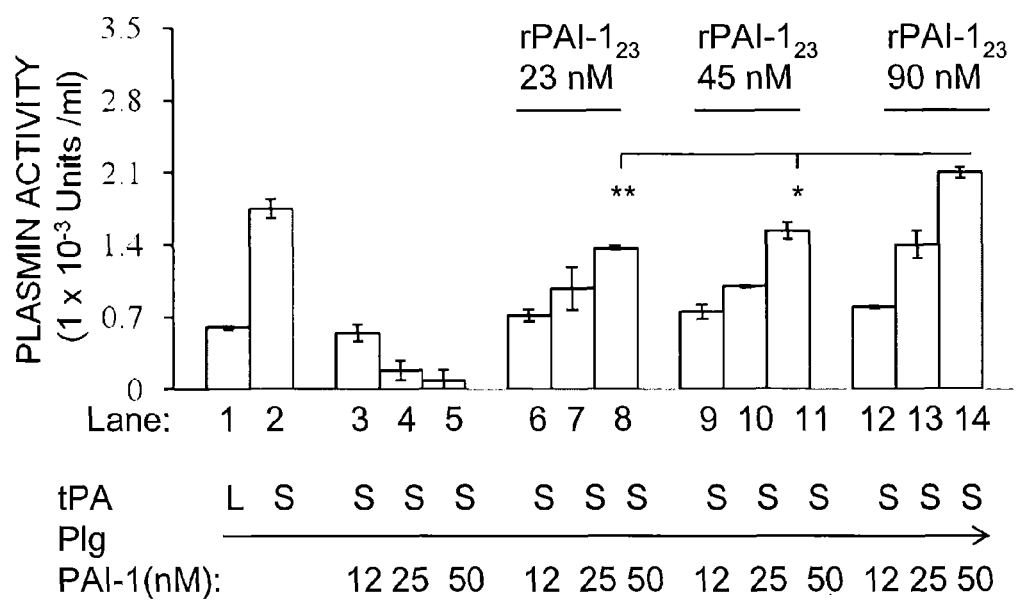

Biochemical studies were performed to investigate if rPAI-$1_{23}$ or PAI-1 binding affinity for plasminogen modifies plasmin activity. One set of reactions allowed varied concentrations of rPAI-$1_{23}$ and PAI-1 to bind plasminogen in a 1 hour, 37° C. incubation before adding tPA for an additional 1 hour incubation (denoted as late (L); FIG. 2A). In a second set of reactions, tPA, plasminogen, rPAI-$1_{23}$ or PAI-1 were added simultaneously (denoted as "simultaneously" (S); FIG. 2B) to a reaction mixture and incubated at 37° C. for 1 hour. A third set of reactions contained tPA, plasminogen, rPAI-$1_{23}$ and PAI-1 added simultaneously to a reaction mixture and incubated for 1 hour at 37° C. (FIG. 2C). Plasmin activity was measured in a chromozym assay.

Notably, plasmin activity was 65% less in the reaction where plasminogen was incubated for 1 hour prior to adding tPA (FIG. 2A, Lane 1) compared to the reaction in which plasminogen and tPA were added simultaneously (Lane 2) (Late, 0.6±0.02 vs. simultaneously, 1.7±0.1×10$^{-3}$ U/ml). Plasmin activity was significantly higher in reactions containing 90 nM rPAI-$1_{23}$ (Lane 8) when compared to the plasminogen/tPA "simultaneous" control (Lane 2, S) (90 nM rPAI-$1_{23}$, 2.7±0.3 vs. plasminogen/tPA (S), 1.7±0.1×10$^{-3}$ U/ml, p=0.006). Unexpectedly, plasmin activity in the "late" reactions containing 50 nM PAI-1 (Lane 5) was significantly higher than the plasminogen/tPA "late" control (Lane 1, L) (plasminogen/tPA (L), 0.6±0.02 vs. 50 nM PAI-1 (L), 1.38±0.06×10$^{-3}$ U/ml, p=0.003).

The second set of reactions, where plasminogen was not pre-bound to rPAI-$1_{23}$ or PAI-1, showed that rPAI-$1_{23}$ at all three tested concentrations does not alter plasmin levels relative to the plasminogen/tPA "S" control (FIG. 2B, Lanes 6-8). PAI-1 inhibited plasmin activity in a dose-dependent manner (Lanes 3-5).

The third set of reactions tested potential opposing effects of rPAI-$1_{23}$ on PAI-1 inhibition of plasmin activity. The results indicated that combining the two PAI-1 isoforms simultaneously with plasminogen and tPA altered the antiproteolytic effects of PAI-1 (FIG. 2C, Lanes 6-14 compared to Lanes 3-5). The increase in plasmin activity occurred in a stepwise fashion that was dependent upon and limited by the concentrations of both molecules. The collective data from this series of experiments showed that rPAI-$1_{23}$ was able to block the inhibitory effects of PAI-1 through binding interactions of both proteins with plasminogen.

Example 10

Increased Proteolytic Activity in rPAI-$1_{23}$-Treated Endothelial Cells Stimulates Collapse of Tubes HUVECs were treated with rPAI-$1_{23}$ to determine if rPAI-$1_{23}$ stimulates plasmin and/or MMP-3 activity in endothelial cells (ECs) and the effect the proteolytic activities have on endothelial cell (EC) tube formation in a 3-D collagen overlay assay. HUVECs grown in medium supplemented with 10% FBS were incubated for 18 hours at 37° C. with rPAI-$1_{23}$, PAI-1 or rPAI-$1_{23}$+PAI-1. Plasminogen (2 nM) was added to the culture medium along with each treatment group. Culture medium was collected at 18 hours of incubation and assayed for plasmin, MMP-3 and PAI-1 activities. Plasmin activity was 2.2-fold greater in culture medium from ECs treated with rPAI-$1_{23}$ compared to PAI-1-treated cells (rPAI-$1_{23}$, 0.6±0.18 vs. PAI-1, 0.27±0.01×10$^{-3}$ U/ml, p=0.01), but was not significantly different from the tPA control (tPA, 0.8±0.15 10$^{-3}$ U/ml, p=NS). Although plasmin activity was increased in the rPAI-$1_{23}$+PAI-1 treatment, the level was not significantly different from the singular treatment groups (rPAI-$1_{23}$+PAI-1, 0.4±0.16 10$^{-3}$ U/ml, NS). MMP-3 activity was 2-fold higher in the medium of rPAI-$1_{23}$-treated cells compared to media from controls (rPAI-$1_{23}$ 0.73±0.1 vs. untreated 0.37±0.04, PAI-1 0.34±0.08 pmoles substrate/minute, p=0.04). PAI-1 activity was significantly reduced in rPAI-$1_{23}$-treated cells compared to untreated and tPA controls (rPAI-$1_{23}$, 14.5±0.7 vs. untreated, 24±1.4 and tPA, 21.5±2 U/ml, p>0.05). PAI-1 added to cells treated with rPAI-$1_{23}$ raised PAI-1 activity to control levels (23.5±0.7 IU).

Next, the effect of rPAI-$1_{23}$-stimulated proteolytic activity on angiogenic EC tube formation was tested in HUVECs embedded in a collagen-1 3-D gel. FGF-2 was added to each collected conditioned medium sample, the mixtures were added to the ECs and incubated for 18 hours before counting complete EC enclosures, the measurement of tube formation. Untreated, rPAI-1$_{23}$— and PAI-1-treated cells had comparable numbers of enclosures in the absence of FGF-2 stimulation. Collagen-embedded tubes stimulated by FGF-2 were significantly inhibited by rPAI-1$_{23}$ and rPAI-1$_{23}$+PAI-1 treatment (rPAI-1$_{23}$, 6±4; rPAI-1$_{23}$+PAI-1, 4±2 vs. FGF-2, 38±8 complete enclosures, p<0.001), while PAI-1 only inhibited 37% of the FGF-2 stimulated tubes (PAI-1, 24±6 complete enclosures, p=NS).

These data provide evidence that rPAI-1$_{23}$-stimulated plasmin and MMP-3 activities contribute significantly to collapse of tubes stimulated by an angiogenic growth factor. The presence of PAI-1 alone does not block the angiogenic stimulation.

Example 11

Vasa Vasorum Form a Plexus-Like Structure in Hypercholesterolemic Mice

DKO mice, fed CH diet for 12 weeks followed by 20 weeks of PD, were treated with either saline or rPAI-1$_{23}$ during the last 6 weeks of PD. Confocal z-stack images of DA whole mounts from mice perfused with FITC-lectin were acquired. Mice that were fed CH for 32 weeks had detectable adventitial vessels, but they did not display a branching pattern. However, mice fed PD and treated with saline had a dense vasa vasorum with a distinct network. The network was present in rPAI-1$_{23}$ treated PD mice, but smaller branches were deteriorating. Images at 63× magnification showed that the vasa vasorum in saline-treated PD mice formed enclosed vascular structures, which were absent in the CH-fed control and were regressing/collapsing in the rPAI-1$_{23}$-treated PD mice. The data showed that the vasa vasorum acquired a different structure in response to the diet-induced disease process that regressed with anti-angiogenic rPAI-1$_{23}$ treatment.

Example 12

FGF-2 Forms a Distinct Pattern in the Adventitia

It has been demonstrated that FGF-2 is the predominant angiogenic growth factor in the DA adventitia of PD-fed mice (Drinane, et al. (2009) supra). Further examination of FGF-2 and vascular endothelial growth factor (VEGF) protein expression in PD-fed mice perfused with FITC-lectin showed that VEGF was mostly undetectable in the adventitial vessels and in rare cases was found randomly distributed in the ECM/BM. On the other hand, FGF-2 was abundantly expressed and formed a distinct pattern in the adventitia of saline-treated PD mice. The vasa vasorum pattern of distribution was quite different; one area was dense and disorganized, while others areas were less dense and more organized. Areas of vasa vasorum disorganization corresponded with areas where FGF-2 was barely detectable. On the other hand, areas with a defined FGF-2 pattern had vessels that became a more organized network. These data indicated that FGF-2 was required for the vasa vasorum to form an organized network.

Example 13

FGF-2 is Required for Vasa Vasorum Plexus Network

To determine if FGF-2 is required for the vasa vasorum to form a distinct network, DKO mice fed PD for 14 weeks were treated with either rPAI-1$_{23}$ or sFGFR1. It was shown herein that the anti-angiogenic rPAI-1$_{23}$ protein causes collapse of the vasa vasorum through a mechanism that increases plasmin activity, therefore this was used as a means of investigating FGF-2 distribution in relationship to loss of vasa vasorum. On the other hand, sFGFR1 serves as a decoy for FGFs and provides a means of examining how the loss of FGF affects the vasa vasorum network. Mice that were CH-fed for 32 weeks or CH-fed for 12 weeks followed by 14 week of PD (TO) were used as controls.

FGF-2 was present in a diffuse pattern in CH-fed mice, lectin-perfused vessels were few in number and did not form a network. After 14 weeks of PD, FGF-2 became more remodeled in the TO group, the vasa vasorum had expanded and were aligning with FGF-2. FGF-2 had developed a distinct pattern of enclosures by 20 weeks of PD and the vessels formed enclosures that were in a pattern similar to FGF-2. Six weeks of rPAI-1$_{23}$ treatment resulted in a significant reduction in detectable FGF-2. Moreover, most vessels have collapsed/regressed and those that remained were aligned with FGF-2. Similarly, FGF-2 and associated vasa vasorum in PD mice treated with soluble FGFR1 were significantly reduced.

The observed differences in FGF-2 and vasa vasorum were verified in measurements of lectin and FGF-2 volume and area in reconstructed confocal z-stacks. There were significant differences between the saline and rPAI-1$_{23}$-treated mice. Lectin volume was 2-fold greater in the PD-fed saline vs. the PD-fed, rPAI-1$_{23}$ treatment group (saline, 0.04±0.007 mm$^3$; rPAI-1$_{23}$, 0.02±0.004 mm$^3$, p=0.03). The difference in FGF-2 volume between the two groups was 2.4-fold (saline, 0.059±0.02 mm$^3$; rPAI-1$_{23}$, 0.025±0.01 mm$^3$, p=0.05). Similarly, the lectin area was 2.3-fold greater in PD-fed saline compared to PD-fed rPAI-1$_{23}$-treated mice (saline, 4±0.2 mm$^2$; rPAI-1$_{23}$, 1.75±0.4 mm$^2$, p<0.001) and the FGF-2 area was 3.3-fold more in the mice treated with saline compared to rPAI-1$_{23}$ (saline, 4.9±0.5 mm$^2$; rPAI-1$_{23}$, 1.48±0.14 mm$^2$, <0.001).

Example 14

Potential FGF-2 Binding Partners

It was contemplated that FGF-2 may require a binding partner to define its distinct pattern of distribution. Perlecan was considered as a potential partner for two reasons. First, it is known to bind FGF-2 (Knox, et al. (2002) *J. Biol. Chem.* 277:14657-14665; Vincent, et al. (2007) *Osteoarthritis Cartilage* 15:752-763). Second, it was shown that rPAI-1$_{23}$-stimulated increases in plasmin and MMP-3 activities degrades perlecan and other key components of the ECM/BM in PD-fed DKO mice. The degradation leads to loss of the supportive scaffold needed for angiogenic vasa vasorum stability, therefore the vessels collapse. Cross sections of the DA from saline and rPAI-1$_{23}$-treated PD DKO mice were probed for perlecan, FGF-2 and CD31 to visualize the distribution of perlecan and FGF-2 in relation to vessels in the adventitia. Co-localization of perlecan with FGF-2 was detected at sites of CD-31$^+$ vascular enclosures in the saline-treated group. However, mice treated with rPAI-1$_{23}$ showed complete loss of perlecan and loss of most well-defined vascular enclosures; FGF-2 was detectable, but lacked a distinct pattern. The images indicated that the vasa vasorum had collapsed/regressed in the absence of perlecan. The angiogenic vessels would not be expected to survive if the ECM/BM scaffold is degraded. To determine if ECs were dying, propidium iodide was injected intraorbitally into mice from both treatment groups. Following perfusion, DA were probed for EC marker, CD31. The saline-treated mice had an intact vasa vasorum plexus, while the ECs in the vasa vasorum of rPAI-1$_{23}$-treated mice were mostly dead.

Example 15

Plasmin Remodels the Angiogenic Vasa Vasorum

As shown herein, elevated plasmin activity in rPAI-1$_{23}$-treated PD-fed DKO mice degrades perlecan, nidogen and fibrin(ogen) to result in collapse of angiogenic vasa vasorum. Therefore, the vasa vasorum structure was examined in PD-fed DKO/PAI-1$^{-/-}$ mice that produced excess plasmin. Mice were maintained on the same diet and treatment schedule as described for PD-fed DKO mice. Reconstructed confocal images of the adventitial vasa vasorum in DA whole mounts showed that the PD-fed DKO mice had a structural hierarchy; there was a large main vessel from which smaller vessels branched and they in turn branched to form a plexus. The vasa vasorum in the DKO, rPAI-1$_{23}$ treatment group had large main vessels, but the plexus was collapsing/regressing. The PD-fed DKO/PAI-1$^{-/-}$ mice treated with saline had an ordered arterial tree with smaller vessels between the larger branches. The smaller vessels appeared to have been a plexus located between and connecting the main branches of an ordered arterial tree. The vessels in the network were undergoing degradation/pruning. On the other hand, the rPAI-1$_{23}$-treated DKO/PAI-1$^{-/-}$ mice had large vessels that did not display a vascular tree or a plexus-like network, but had collapsed due to loss of the network between branches. The difference in plasmin activity between the DKO/PAI-1$^{-/-}$ saline and rPAI-1$_{23}$ treatment groups was 1.8-fold (rPAI-1$_{23}$, 1.2±0.06×10$^{-3}$ vs. saline, 0.65±0.04×10$^{-3}$ units/ml, p<0.05). These data indicated that ECM/BM supporting the plexus was a plasmin substrate thus making plasmin a key protease in regulating the stability of the angiogenic vasa vasorum.

The data herein supports a model where the DA 1$^{st}$ order vasa vasorum branches at several sites, which are predictably at intercostals. The branches continue to expand into a tree-like structure with the angiogenic 2$^{nd}$ order vasa vasorum (plexus) occupying the space between the large vessels to stabilize the vascular tree. When the expanded vasculature is no longer needed or is inhibited, the 2$^{nd}$ order vasa vasorum collapse leaving behind a normal 1$^{st}$ order structure. In order for this regulation of vasa vasorum expansion and regression to occur in response to the needs of the vessel wall requires FGF-2 and orchestration of matrix remodeling.

---

What is claimed is:

1. A method for increasing plasmin activity comprising administering to a subject in need thereof an effective amount of recombinant plasminogen activator inhibitor type 1 isoform 23 (rPAI-1$_{23}$) that increases plasmin activity and determining plasmin activity in the subject administered the rPAI-1$_{23}$, wherein the rPAI-1$_{23}$ is administered at a dose in the range of approximately 2.5 µg/kg/day to 20 µg/kg/day.

2. The method of claim 1, wherein rPAI-1$_{23}$ is set forth in SEQ ID NO:5, SEQ ID NO:6, SEQ ID NO:7 or SEQ ID NO:8.

3. The method of claim 1, wherein the effective amount achieves a ratio of rPAI-1$_{23}$ to PAI-1 in the range of approximately 1:2 to 3:1.

* * * * *

UNITED STATES PATENT AND TRADEMARK OFFICE
CERTIFICATE OF CORRECTION

| | | |
|---|---|---|
| PATENT NO. | : 9,078,904 B2 | Page 1 of 1 |
| APPLICATION NO. | : 13/982830 | |
| DATED | : July 14, 2015 | |
| INVENTOR(S) | : Mary Jo Mulligan-Kehoe | |

It is certified that error appears in the above-identified patent and that said Letters Patent is hereby corrected as shown below:

In the Specification

Column 1, please delete Lines 13-15 and insert in its place the following:
--This invention was made with government support under grant number R01 HL069948 awarded by the National Institutes of Health. The government has certain rights in the invention.--

Signed and Sealed this
Twenty-eighth Day of April, 2020

Andrei Iancu
*Director of the United States Patent and Trademark Office*